(12) United States Patent
Gaur et al.

(10) Patent No.: US 6,933,274 B2
(45) Date of Patent: *Aug. 23, 2005

(54) METHODS FOR TREATMENT OF DIABETES USING A PEPTIDE ANALOGUES OF INSULIN

(75) Inventors: Amitabh Gaur, San Diego, CA (US); Nicholas Ling, San Diego, CA (US); Paul J. Conlon, Solana Beach, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/339,160

(22) Filed: Jan. 8, 2003

(65) Prior Publication Data

US 2004/0082503 A1 Apr. 29, 2004

Related U.S. Application Data

(63) Continuation of application No. 09/787,140, filed as application No. PCT/US99/03915 on Feb. 23, 1999, now Pat. No. 6,562,942, which is a continuation-in-part of application No. 09/028,156, filed on Feb. 23, 1998, now abandoned.

(51) Int. Cl.[7] .................... C07K 11/00; A61K 38/28; A61K 38/10
(52) U.S. Cl. .............. 514/2; 514/3; 514/13; 514/14; 530/303; 530/326; 435/69.4
(58) Field of Search .................. 530/303, 326; 514/2, 3, 13, 14, 12; 435/69.4

(56) References Cited

U.S. PATENT DOCUMENTS

| | | | |
|---|---|---|---|
| 5,597,796 A | 1/1997 | Brange | 514/3 |
| 6,197,926 B1 | 3/2001 | Gaur et al. | 530/303 |
| 6,562,942 B1 * | 5/2003 | Gaur et al. | 530/303 |

FOREIGN PATENT DOCUMENTS

| | | |
|---|---|---|
| WO | WO 96/04307 | 2/1996 |
| WO | WO 97/02043 | 1/1997 |
| WO | WO 99/42482 | 8/1999 |

OTHER PUBLICATIONS

Daniel and Wegmann, "Intranasal Administration of Insulin Peptide B: 9–23 Protects NOD Mice from Diabetes," *Annals of the New York Academy of Sciences* 778: 371–372, 1996.

Daniel and Wegmann, "Protection of nonobese diabetic mice from diabetic by intranasal or subcutaneous administration of insulin peptide B–(9–23)," *Proc. Natl. Acad. Sci. USA 93*: 956–960, Jan. 1996.

Gattner et al., "The Preparation of Two Mutant Forms of Human Insulin, Containing Leucine in Position B24 or B25, by Enzyme–Assisted Synthesis," *Hoppe–Seyler's Z. Physiol. Chem. 361*: 1135–1138, 1980.

Jonczyk et al., "Preparation and Biological Properties of [Leu$^{B24}$,Leu$^{B25}$] Human Insulin," *Hoppe–Seyler's Z. Physiol. Chem. 362*: 557–561, 1981.

Katsoyannis et al., "Insulin Peptides. XIX. The Synthesis of Two Nanopeptide Derivatives Related to the N Terminus of the B Chain of Insulin from Various Species (Positions 1–9)," *Journal of the American Chemical Society 93*(22): 5862–5864, Nov. 3, 1971.

Kristensen, C. et al., "Alanine Scanning Mutagensis of Insulin," *Journal of Biological Chemistry 272*(20): 12978–12983, May 16, 1997.

Lenz et al., "Semisynthetic Des–(B27–B30)–insulins with Modified B26–Tyrosine," *Biol. Chem. Hoppe–Seyler 372*: 495–504, Jul. 1991.

Leyer et al., "The role of the C–terminus of the insulin B–chain in modulating structural and functional properties of the hormone," *Int. J. Peptide Protein Res. 46*: 397–407, 1995.

Losse et al., "Synthese Eines Kondensationsfähigen Insulin–B15–20–Hexapeptidderivates," *Tetrahedron 33*: 1817–1819, 1977.

Polanski et al., "Oral Administration of the Immunodominant B–chain of Insulin Reduces Diabetes in a Co–transfer Model of Diabetes in the NOD Mouse and is Associated with a Switch from Th1 to Th2 Cytokines," *Journal of Autoimmunity 10*: 339–346, 1997.

Riemen et al., "Preparation of Semisynthetic Insulin Analogues from Bis(tert–butyloxycarbonyl)–desoctapeptide–insulin Phenylhydrazide Importance of the Aromatic Region B24–B26," *Biochemistry 22*: 1507–1515, 1983.

Schwartz et al., "Insulin Peptides. Part XXIII. The Synthesis of a Hexadecapeptide Derivative Related to the B Chain of Human Insulin," *J. Chem. Soc. Perkin I*: 2890–2894, 1973.

Schwartz and Katsoyannis, "Synthesis of Des(tetrapeptide B$^{1-4}$) and Des(pentapeptide B$^{1-5}$) Human Insulins. Two Biologically Active Analogues," *Biochemistry 17*(21): 4550–4556, 1978.

Schwartz et al., "[12–Asparagine–B] Human Insulin," *Int. J. Peptide Protein Res. 17*: 243–255, 1981.

(Continued)

*Primary Examiner*—Jon Weber
*Assistant Examiner*—Chih-Min Kam
(74) *Attorney, Agent, or Firm*—Seed IP Law Group

(57) ABSTRACT

The present invention is directed toward peptide analogues of insulin B chain that are generally derived from peptides comprising residues 9 to 23 of the native B chain sequence. The analogues are altered from the native sequence at position 12, 13, 15 and/or 16, and may be additionally be altered at position 19 and/or other positions. Pharmaceutical compositions containing these peptide analogues are provided. The peptide analogues are useful for treating and inhibiting the development of diabetes.

22 Claims, 15 Drawing Sheets

OTHER PUBLICATIONS

Svoboda et al., "Semisynthetic Insulin Analogues Modified in Positions B24, B25, and B29," *Biol. Chem. Hoppe–Seyler* 375:373–378, Jun. 1994.

Toyota et al., "Effects of Hexapeptide, a Compound Analogous to Insulin B Chain Fragment B–21–26(DP–432) on the Glucose Uptake into the Perfused Hind Limb of Rats," *Horm. Metab. Res. 10*: 17–20, 1978.

Wang et al., "Insulin Analogues with Modifications in the β–Turn of the B–Chain," *Journal of Protein Chemistry 10*(3): 313–324, 1991.

Weitzel et al., "Structure and Activity of Insulin, XVI[1–6], Semisyntheses of Desheptapeptide-(B24–30)– up to Destripeptide-(B28–30)– Insulin with Lysine or Alanine in Place of Arginine in Position B22: Influence on the Three–Step–Increase of Activity in Positions B24–B26 (Phe–Phe–Tyr)," *Hoppe–Seyler's Z. Physiol. Chem. 359*: 945–958, Aug. 1978.

Yueh–ting et al., "Synthesis of the Peptide Fragments of the B–Chain of Insulin," *Scientia Sincia 15*(2): 221–230, 1966.

* cited by examiner

INSULIN B 9-23

9 weekly treatments with 400 µg
of peptides starting on day 24

METHODS FOR TREATMENT OF DIABETES USING A PEPTIDE ANALOGUES OF INSULIN

This application is a continuation of U.S. application Ser. No. 09/787,140, filed Jun. 7, 2001, now U.S. Pat. No. 6,562,942, which is a 371 of PCT/US99/03915, filed Feb. 23, 1999, which is a continuation-in-part of U.S. application Ser. No. 09/028,156, filed Feb. 23, 1998, now abandoned.

BACKGROUND OF THE INVENTION

1. Field of the Invention

The present invention relates generally to peptide analogues of insulin, and more specifically to methods for treating diabetes using peptide analogues derived from residues 9–23 of human insulin B chain.

2. Description of the Related Art

Insulin dependent diabetes mellitus (IDDM) is an organ specific aautoimmune disease affecting close to a million people in different age groups in the United States. The disease is characterized by extensive destruction of the insulin producing beta cells in the pancreatic islets and dysregulation of glucose metabolism leading to frank diabetes. The defining feature of IDDM is the lymphocytic infiltration of the islets. Among the invading cells, T cells appear to be one of the major mediators of autoimmune destruction.

Type I diabetes is further characterized by increased levels of antibodies to various islet associated antigens, including insulin, GAD65, GAD67 and ICA512. These antibodies can be detected much before frank disease, and an immune response to such antigens can be used as a predictor for impending diabetes in patients with susceptible genetic (HLA) haplotypes.

Currently, patients are dependent on insulin injections to maintain normoglycemia. Insulin is a polypeptide hormone consisting of two disulfide-linked chains, an A chain consisting of 21 amino acid residues and a B chain of 30 residues. While administration of insulin provides significant benefits to patients suffering from diabetes, the short serum half-life of insulin creates difficulties for maintaining proper dosage. The use of insulin also can result in a variety of hypoglycemic side-effects and the generation of neutralizing antibodies.

In view of the problems associated with existing treatments of diabetes, there is a compelling need for improved treatments that are more effective and are not associated with such disadvantages. The present invention exploits the use of peptide analogues which antagonize a T cell response to insulin to effectively treat diabetes, while further providing other related advantages.

BRIEF SUMMARY OF THE INVENTION

The present invention provides compounds and methods for treating and preventing diabetes. Within certain aspects, the present invention provides peptide analogues comprising residues 9 to 23 of human insulin B chain (SEQ ID NO:2), wherein the peptide analogue differs in sequence from native human insulin B chain residues 9 to 23 due to substitutions at between 1 and 4 amino acid positions. Such substitutions may be made at one or more residues selected from the group consisting of residues 12, 13, 15 and 16, with or without additional substitutions at other residues. Within certain preferred embodiments, such substitutions may occur at two or three amino acid residues within residues 9 to 23 of insulin B chain. Substitutions may also occur at residue 19. Substitutions are preferably non-conservative, and analogues wherein residue 12, 13, 15, 16 and/or 19 are altered (to, for example, alanine) are preferred. Analogues further comprising residue 24 of insulin B chain are also preferred. In certain other embodiments, the peptide analogues comprise no more than 18 residues, no more than 16 residues or no more than 15 residues of human insulin B chain.

Within further embodiments, the peptide analogues consist essentially of residues 9 to 23 or 9 to 24 of human insulin B chain (SEQ ID NO:2), wherein the peptide analogue differs in sequence from native human insulin B chain residues 9 to 23 due to substitutions at between 1 and 4 amino acid positions, and wherein at least one substitution occurs at a residue selected from the group consisting of residues 12, 13, 15 and 16.

Within further aspects, pharmaceutical compositions are provided, comprising a peptide analogue as described above in combination with a physiologically acceptable carrier or diluent.

The present invention further provides methods for treating and/or inhibiting the development of diabetes, comprising administering to a patient a therapeutically effective amount of a pharmaceutical composition as described above.

These and other aspects of the invention will become evident upon reference to the following detailed description and attached drawings. In addition, various references are set forth below which describe in more detail certain procedures or compositions. These references are incorporated herein by reference in their entirety as if each were individually noted for incorporation.

DETAILED DESCRIPTION OF THE INVENTION

Prior to setting forth the present invention, it may be helpful to an understanding thereof and to provide definitions of certain terms that are used herein.

"Insulin B chain" refers to a 30 amino acid polypeptide present as one of the two disulfide-linked polypeptides that make up insulin. The sequence of human insulin B chain is provided in SEQ ID NO:1, and the sequence of residues 9–23 of human B chain is provided in FIG. 1 and SEQ ID NO:2.

"Peptide analogues" of the insulin B chain comprise at least 15 amino acid residues derived from residues 9–23 of human insulin B chain (SEQ ID NO:2), with at least one difference in amino acid sequence between the analogue and the native B chain. Within a peptide analogue, at least one difference in amino acid sequence occurs at residue 12, 13, 15 and/or 16. In addition, residue 19 may be substituted, and other alterations are possible. Preferably, a peptide analogue contains between 1 and 4 substitutions within residues 9–23, relative to a native insulin B chain (9–23) sequence, although a greater number of substitutions (e.g., 5 or 6) may be possible. Additional residues derived from insulin B chain may be included, up to the full 30 residues of native B chain, preferably up to a total of 25 residues, more preferably up to a total of 16 or 18 residues of the peptide analogue. Within a preferred embodiment, residue 24 of insulin B chain is also included in the peptide analogue. Sequences that are not derived from insulin B chain may, but need not, be present at the amino and/or carboxy terminus of the peptide analogue. Such sequence(s) may be used, for example, to facilitate synthesis, purification or solubilization of the peptide analogue.

Unless otherwise indicated, a named amino acid refers to the L-form. An L-amino acid residue within the native peptide sequence may be altered to any one of the 20 L-amino acids commonly found in proteins, any one of the corresponding D-amino acids, rare amino acids, such as 4-hydroxyproline or hydroxylysine, or a non-protein amino acid, such as β-alanine or homoserine. Also included with the scope of the present invention are analogues comprising amino acids that have been altered by chemical means such as methylation (e.g., α-methylvaline); amidation of the C-terminal amino acid by an alkylamine such as ethylamine, ethanolamine or ethylene diamine; and/or acylation or methylation of an amino acid side chain function (e.g., acylation of the epsilon amino group of lysine).

Figures 1, 2:
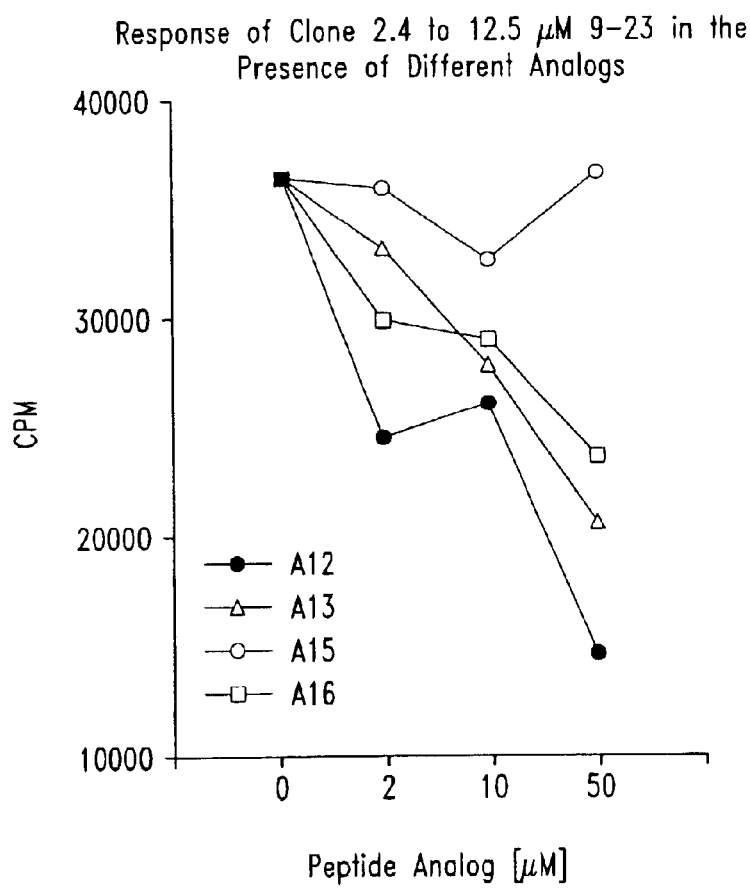
FIG. 1 depicts the amino acid sequence of residues 9–23 of insulin B chain (SEQ ID NO:2).
FIG. 2 is a graph showing the proliferative response (measured in cpm) of a NOD mouse T cell clone to a native insulin B chain (9–23) peptide in the presence of varying amounts of representative peptide analogues, in which different residues are substituted with alanine, as indicated.

"Residue 12," "residue 13," "residue 15," "residue 16" and "residue 19" (also called position 12, position 13, position 15, position 16 and position 19, respectively) refer to amino acids 12, 13, 15, 16 and 19 of insulin B chain as displayed in FIG. 1. More specifically, the numbering system for these residues relates to the amino acid position within the native human protein, regardless of the length of the peptide analogue or the amino acid position within the analogue. Peptide analogues having an alanine substitution at residues 12, 13, 15 or 16 are referred to as the A12, A13, A15 or A16 analogues, respectively.

Peptide Analogues of Insulin B Chain

As noted above, the present invention provides peptide analogues comprising at least residues 9–23 of human insulin B chain and including an alteration of the naturally occurring L-valine at position 12, L-glutamate at position 13, L-leucine at position 15 and/or L-tyrosine at position 16, to another amino acid. In one embodiment, peptide analogues contain additional alterations of one to three L-amino acids at positions 12, 13, 15, 16 and/or 19 of insulin B chain. Preferably, the peptide analogues contain two or three alterations in which one of the substituted residues is at position 19.

The portion of a peptide analogue that is derived from insulin B chain is typically 15–30 residues in length, preferably 15–18 residues in length, and more preferably 15–16 residues in length. Particularly preferred peptide analogues contain 15 amino acids derived from insulin B chain.

As noted above, peptide analogues comprising any amino acid alteration(s) at the positions recited above are within the scope of this invention. Preferred peptide analogues contain non-conservative substitutions (i.e., alterations to amino acids having differences in charge, polarity, hydrophobicity and/or bulkiness). Particularly preferred analogues contain alterations of one or more residues to alanine.

Peptide analogues may be synthesized by standard chemistry techniques, including automated synthesis. In general, peptide analogues may be prepared by solid-phase peptide synthesis methodology which involves coupling each protected amino acid residue to a resin support, preferably a 4-methyl-benzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminus. Side-chain functional groups may be protected as follows: benzyl for serine and threonine; cyclohexyl for glutamic acid and aspartic acid; tosyl for histidine and arginine; 2-chlorobenzyloxycarbonyl for lysine; and 2-bromobenzyloxycarbonyl for tyrosine. Following coupling, the t-butyloxycarbonyl protecting group on the alpha amino function of the added amino acid may be removed by treatment with trifluoroacetic acid followed by neutralization with di-isopropyl ethylamine. The next protected residue is then coupled onto the free amino group, propagating the peptide chain. After the last residue has been attached, the protected peptide-resin is treated with hydrogen fluoride to cleave the peptide from the resin and deprotect the side chain functional groups. Crude product can be further purified by gel filtration, HPLC, partition chromatography or ion-exchange chromatography, using well known procedures.

Peptide analogues within the present invention (a) should not stimulate NOD mouse T cell clones specific to the native insulin B chain (9–23) peptide (SEQ ID NO:2), or should stimulate such clones at a level that is lower than the level stimulated by the native peptide; (b) should not stimulate insulin B chain (9–23) specific human T cells from patients; (c) should be immunogenic in the NOD mouse; (d) should reduce the incidence of diabetes in NOD mice and (e) may inhibit a response of T cell clones specific to the native insulin B chain (9–23) peptide (SEQ ID NO:2). Thus, candidate peptide analogues may be screened for their ability to treat diabetes by assays measuring T cell proliferation, immunogenicity in NOD mice and the effect on the incidence of the disease in NOD mice. Certain representative assays for use in evaluating candidate peptide analogues are discussed in greater detail below. Those analogs that satisfy the above criteria are useful therapeutics.

Candidate peptide analogues may initially be tested for the ability to stimulate T cells specific to the native insulin B chain (9–23) peptide (SEQ ID NO:2) (from clonal cell lines or isolated from patients). Such tests may be performed using a direct proliferation assay in which native B chain (9–23) reactive T cell lines or T cells isolated from patients are used as target cells. T cell lines may generally be established, using well known techniques, from lymph nodes taken from rats injected with B chain (9–23). Lymph node cells may be isolated and cultured for 5 to 8 days with B chain (9–23) and IL-2. Viable cells are recovered and a second round of stimulation may be performed with B chain (9–23) and irradiated splenocytes as a source of growth factors. After 5 to 6 passages in this manner, the proliferative potential of each cell line is determined. To perform a proliferation assay, B chain (9–23)-reactive T cell lines may be cultured for three days with various concentrations of peptide analogues and irradiated, autologous splenocytes. After three days, 0.5–1.0 $\mu$Ci of [$^3$H]-thymidine is added for 12–16 hours. Cultures are then harvested and incorporated counts determined. Mean CPM and standard error of the mean are calculated from triplicate cultures. Peptide analogues yielding results that are less than three standard deviations of the mean response with a comparable concentration of B chain (9–23) are considered non-stimulatory. Peptide analogues which do not stimulate proliferation at concentrations of less than or equal to 20–50 $\mu$M are suitable for further screenings.

Candidate peptides that do not stimulate B chain (9–23) specific T cells, and preferably inhibit a response of such T cells in vitro, are further tested for their immunogenicity in the NOD mouse. Briefly, groups of NOD mice may be immunized with 100–400 $\mu$g of the candidate peptides subcutaneously in mannitol acetate buffer three times within a period of 10–15 days. Following the last immunization, lymph node cells and/or spleen cells may be used in a proliferation assay in which different concentrations of the immunizing peptide are cultured with the cells for 34 days. The last 18 hours of culture may be performed with tritiated thymidine. Cells may then be harvested and counted in a scintillation counter, and the proliferative response may be expressed as CPM±SEM. Candidate peptides that induce a proliferation that is at least 2-fold higher than the background (no antigen) at 25 $\mu$M of the peptide are considered to be immunogenic. Alternatively, the candidate peptide analogue is considered immunogenic if it elicits a proliferative response following immunization of the NOD mice in complete Freund's adjuvant. The draining lymph node cells or spleen cells, when cultured in the presence of the immunizing analogue, should induce a proliferation that is at least 2-fold higher than the background (no antigen) at 25 $\mu$M of the peptide.

Candidate peptides that can inhibit proliferation by B chain (9–23) are further tested for the ability to reduce the incidence of diabetes in NOD mice. Briefly, peptides may be administered to NOD mice in soluble form or emulsified with, for example, incomplete Freund's adjuvant (IFA). Typically, weekly administration of about 400 $\mu$g of peptide is sufficient. The incidence of diabetes in the treated mice, as well as in untreated or control mice, is then evaluated by weekly monitoring of blood glucose levels. A value of 200 mg/dl or more of blood glucose on two consecutive occasions is generally considered indicative of the appearance of diabetes. Peptide analogues should result in a statistically significant decrease in the percent of NOD mice afflicted with diabetes within a monitoring period of up to about 25 weeks.

As noted above, peptide analogues may also inhibit the response of B chain (9–23) specific human T cells in vitro. Such inhibition may be measured by a competition assay in which candidate peptide analogues are tested for the ability to inhibit T cell proliferation induced by native B chain (9–23) (SEQ ID NO:2). In such an assay, antigen presenting cells are first irradiated and then incubated with the competing peptide analogue and the native B chain (9–23) peptide. T cells are then added to the culture. Various concentrations of candidate peptide analogues are included in cultures which may be incubated for a total of 4 days. Following the incubation period, each culture is pulsed with, for example, 1 $\mu$Ci of [$^3$H]-thymidine for an additional 12–18 hours. Cultures may then be harvested on fiberglass filters and counted as above. Mean CPM and standard error of the mean can be calculated from data determined in triplicate cultures. Peptide analogues that reduce proliferation by at least 25% at a concentration 20–50 $\mu$M are preferred.

Treatment and Prevention of Diabetes

As noted above, the present invention provides methods for treating and preventing Type I diabetes by administering to the patient a therapeutically effective amount of a peptide analogue of insulin B chain as described herein. Diabetic patients suitable for such treatment may be identified by criteria accepted in the art for establishing a diagnosis of clinically definite diabetes. Such criteria may include, but are not limited to, low (less than tenth or first percentile of controls) first phase insulin secretion following an intravenous glucose tolerance test (IVGTT) or the persistence of high titer antibodies to islet antigens such as insulin, GAD65 and/or ICA512.

Patients without clinically definite diabetes who may benefit from prophylactic treatment may generally be identified by any predictive criteria that are accepted in the art. Patients who are not frankly diabetic may be predicted to develop diabetes in the coming years (1–5 yrs) based upon the following criteria: i) family history—first degree relatives are automatically in the high risk group unless they have a protective HLA allele; ii) genetic make-up—i.e., the presence or absence of an HLA allele that is associated with a high risk of diabetes (e.g., DR3/4; DQ8); iii) presence or absence of high titer autoantibodies in their blood to any or all of the antigens: insulin, GAD65 and/or ICA 512; and iv) intravenous glucose tolerance test (IVGTT): low first-phase insulin secretion, usually defined as below the tenth or first percentile of normal controls, typically precedes the development of type I diabetes by 1–5 years. In general, several of the above criteria may be considered. For example, the chances of developing diabetes in 5 years for a first degree relative of an individual with diabetes are estimated to be: 100% for relatives with all 3 autoantibodies listed above; 44% for relatives with 2 antibodies; 15% for relatives with one antibody; and 0.5% for relatives with no antibodies. Among 50 first degree relatives of patients with Type I diabetes followed to the onset of diabetes, 49/50 expressed one or more of the above listed autoantibodies.

Effective treatment of diabetes may be determined in several different ways. Satisfying any of the following criteria, or other criteria accepted in the art, evidences effective treatment. Criteria may include, but are not limited to, delay in developing frank hyperglycemia, lowered frequency of hyperglycemic events and/or prolongation of normal levels of C-peptide in the blood of the patients.

Peptide analogues of the present invention may be administered either alone, or as a pharmaceutical composition. Briefly, pharmaceutical compositions of the present invention may comprise one or more of the peptide analogues described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, sustained delivery systems or other immunopotentiators.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulated as a lyophilizate, utilizing appropriate excipients which provide stability as a lyophilizate and/or following rehydration.

Pharmaceutical compositions of the present invention may be administered in a manner appropriate to the disease to be treated (or prevented). The quantity and frequency of administration will be determined by such factors as the condition of the patient, and the type and severity of the patient's disease. Within particularly preferred embodiments of the invention, the peptide analogue may be administered at a dosage ranging from 0.1 to 100 mg/kg, although appropriate dosages may be determined by clinical trials. Patients may be monitored for therapeutic effectiveness by delay in progression to frank diabetes and sustained use of insulin for maintaining normoglycemia as described above.

The following examples are offered by way of illustration and not by way of limitation.

EXAMPLE 1

Preparation of Peptides

This Example illustrates the synthesis of representative peptide analogues.

Peptides were synthesized by solid phase methodology on a peptide synthesizer (Beckman model 990). Peptides with an amidated carboxyl-terminus were prepared with a p-methylbenzhydrylamine resin (MBHA resin); for peptides with a free carboxyl-terminus, a Merrifield resin coupled with the appropriately protected amino acid was used. Both resins were obtained from Bachem Fine Chemicals (Torrance, Calif.). Derivatized amino acids (Bachem Fine Chemicals) used in the synthesis were of the L-configuration unless specified otherwise, and the N-alpha-amino function protected exclusively with the t-butyloxycarbonyl group. Side-chain functional groups were protected as follows: benzyl for serine and threonine; cyclohexyl for glutamic acid and aspartic acid; tosyl for histidine and arginine; 2-chlorobenzyloxycarbonyl for lysine and 2-bromobenzyloxycarbonyl for tyrosine. Coupling of the carboxyl-terminal amino acid to the MBHA resin was carried out with dicyclohexylcarbodiimide and the subsequent amino acids were coupled with dicyclohexylcarbodiimide according to. Ling et al. (*Proc. Natl. Acad. Sci. USA* 81: 4302, 1984). After the last amino acid was incorporated, the t-butyloxycarbonyl protecting group was removed and the peptide-resin conjugate treated with a mixture of 14 ml hydrofluoric acid (HF), 1.4 ml anisole, and 0.28 ml methylethyl sulfide per gram of resin conjugate at −20° C. for 0.5 hr and at 0° C. for 0.5 hr. HF was removed in vacuum at 0° C., and the resulting peptide and resin mixture was washed twice with diethyl ether and twice with chloroform and diethyl ether alternately. The peptide was extracted five times with 2 M acetic acid, and the extract lyophilized. The lyophilized product was first purified on a column of Sephadex G-25 fine (Pharmacia-LKB, Piscataway, N.J.) developed in 30% acetic acid to remove the truncated fragments and inorganic salts (Ling et al., 1984). Next, peptides were further purified by CM-32 carboxymethylcellulose cation-exchange chromatography (Ling et al., 1984). Final purification was achieved by partition chromatography on Sephadex G-25 fine (Ling et al., 1984). Alternatively, the crude peptide could be purified by preparative HPLC on a Biotage KP-100 gradient HPLC system. The synthetic product was characterized by amino acid analysis, mass spectrometric analysis and reversed-phase HPLC.

EXAMPLE 2

Long-Term T Cell Lines

This Example illustrates the preparation of long-term insulin-specific NOD T cell lines.

Insulin specific NOD T cell lines were established by culturing lymphocytes isolated from islet-infiltrating populations by in vitro stimulation with either porcine insulin at 25 µg/ml and irradiated NOD islet cells in the presence of irradiated NOD spleen cells as antigen presenting cells and cytokines. To obtain the infiltrating lymphocytes the following procedures were performed (see Wegmann et al., *Eur. J. Immunol.* 24: 1853, 1994): the pancreas from the NOD mouse was digested with collagenase and individual islets were isolated manually. The infiltrating lymphocytes were then obtained by mild trypsin digestion of the islets. The insulin specific T cell lines or clones were propagated by serial stimulation in the presence of NOD spleen cells, porcine insulin and lymphokines. Clones were obtained by limiting dilution of the B chain (9–23) specific T cell lines in the presence of the antigen presenting cells and porcine insulin at 25 µg/ml. Wells with a growing population of cells following limiting dilution were expanded in appropriate medium, and after one cycle of growth were tested for reactivity to the B chain (9–23) peptide of insulin by evaluating the proliferative response.

EXAMPLE 3

Effect of Peptide Analogues on Proliferation of Insulin-Specific NOD T Cell Clones This Example illustrates the effect of representative peptide analogues on T cell proliferation.

Insulin B chain (9–23) (SEQ ID NO:2) specific mouse (NOD) T cell clones were isolated from infiltrated islets as described in Example 2. Peptide analogues with single alanine substitutions were prepared as described in Example 1. The effect of each analogue on T cell proliferation was then evaluated using an assay performed in 96-well flat bottom microtiter plates (see Daniel et al., *Eur. J. Immunol.* 25: 1056, 1995). Briefly 25,000 T cell clones along with 1 million irradiated NOD spleen cells were cultured in the presence of 50 µg/ml of insulin B chain 9–23 peptide or any of the alanine substituted peptides listed below in triplicate sets. The plates were incubated for a total of 72 hours in 7% carbon dioxide atmosphere with a pulse of 1 µCi/well of tritiated thymidine for the last 6–8 hours of culture. Cells were harvested on a glass fiber filter and the associated radioactivity was counted in a liquid scintillation counter. Results are expressed as mean counts per minute of triplicate wells.

The data obtained from five separate T cell clones showed either a lack of proliferation or significantly reduced proliferation (relative to the 9–23 native peptide of insulin B chain; SEQ ID NO:2) in the presence of the following alanine substituted analogues: A12, A13, A15, A16, A17, and A18. These data are presented in Tables 1 and 2, below.

TABLE 1

RESPONSE (CPM) OF INSULIN SPECIFIC NOD T CELL CLONES

| Modified Position | Native Residue | Substitution | T cell clone | |
|---|---|---|---|---|
| | | | PD6-4.3 | PD12-2.40 |
| 9 | S | A | 12861 | 42234 |
| 10 | H | A | 12507 | 1409 |
| 11 | L | A | 14148 | 2594 |
| 12 | V | A | 8292 | 671 |
| 13 | E | A | 142 | 519 |
| 14 | A | none | | |
| 15 | L | A | 161 | 1422 |
| 16 | Y | A | 98 | 539 |
| 17 | L | A | 553 | 19321 |
| 18 | V | A | 234 | 44785 |
| 19 | C | A | 7678 | 34212 |
| 20 | G | A | 2440 | 38685 |
| 21 | E | A | 91 | 39087 |
| 22 | R | A | 6555 | 51722 |
| 23 | G | A | 14304 | 75441 |
| no antigen | | | 163 | 682 |
| Native 9–23 | | | 10463 | 32221 |

TABLE 2

RESPONSE (CPM) OF INSULIN SPECIFIC MURINE, NOD T CELL CLONES

| Modified Position | Native Residue | Substitution | T Cell Clone | | |
|---|---|---|---|---|---|
| | | | PD12-4.4 | PD12-4.29 | PD12-4.34 |
| 9 | S | A | 1000 | 18422 | 259 |
| 10 | H | A | 823 | 15484 | 356 |
| 11 | L | A | 474 | 18416 | 190 |
| 12 | V | A | 1129 | 15041 | 194 |
| 13 | E | A | 373 | 891 | 179 |
| 14 | A | A | | | |
| 15 | L | none | 675 | 809 | 191 |
| 16 | Y | A | 779 | 636 | 202 |
| 17 | L | A | 332 | 1460 | 4360 |
| 18 | V | A | 225 | 1193 | 721 |
| 19 | C | A | 4295 | 6054 | 689 |
| 20 | G | A | 1323 | 13736 | 466 |
| 21 | E | A | 7900 | 4904 | 773 |
| 22 | R | A | 1313 | 12635 | 1555 |
| 23 | G | A | 3228 | 18422 | 791 |
| no antigen | | | 350 | 789 | 231 |
| Native 9–23 | | | 10000 | 14820 | 3614 |

Table 3 shows the response of four different NOD derived T cell clones to the double alanine substituted peptide analog A16, A19 (NBI-6024; 16Y>A/19C>A). NOD T cell clones were incubated in the presence of 50 $\mu$M of either the native B chain (9–23) peptide or NBI-6024. The data in Table 3 represent the mean of triplicate sample±standard error of the mean. Within Table 3, S.I. (Stimulation Index)=proliferation (cpm) in the presence of the peptide/proliferation (cpm) in medium alone. These data show a significant response when the cells were cultured with the native B chain (9–23) peptide, but little or no proliferation over medium only (background) in the presence of NBI-6024.

TABLE 3

PROLIFERATIVE RESPONSE OF INSULIN B CHAIN (9–23) SPECIFIC MURINE T CELL CLONES TO 50 $\mu$M OF B CHAIN (9–23) OR THE ANALOGUE $A^{16,19}$ (NBI-6024)

| T Cell Clone | Exp. No. | Medium Only | Insulin B Chain (9–23) | | NBI-6024 ($A^{16,19}$) | |
|---|---|---|---|---|---|---|
| | | | Mean cpm ± sem | S.I. | cpm ± sem | S.I. |
| PD12-2.35 | 1 | 688 ± 227 | 120,886 ± 7,171 | 175.7 | 841 ± 88 | 1.22 |
| | 2 | 493 ± 20 | 100,521 ± 1,581 | 203.89 | 452 ± 179 | 0.91 |
| PD12-2.40 | 1 | 170 ± 8 | 16,730 ± 3,835 | 98.4 | 272 ± 34 | 1.16 |
| | 2 | 1,834 ± 638 | 176,359 ± 36,306 | 96.16 | 1,863 ± 451 | 1.01 |
| PD12-4.1 | 1 | 215 ± 17 | 28,593 ± 4664 | 132.99 | 566 ± 30 | 2.63 |
| PD12-4.9 | 1 | 9,111 ± 1,889 | 45,541 ± 5,222 | 4.99 | 12,313 ± 1,372 | 1.35 |
| | 2 | 7,202 ± 2,773 | 65,624 ± 4,979 | 9.1 | 6,171 ± 725 | 0.85 |

EXAMPLE 4

Antagonism of T Cell Proliferation Assay

This Example illustrates the inhibition of the response of B chain (9–23) specific mouse T cell clones to the insulin B chain (9–23) peptide by representative peptide analogues.

Peptide analogues of B chain (9–23) containing alanine substitutions at residue 12, 13, 15 or 16 or the doubly substituted peptide at positions 16 and 19 ($A^{16,19}$; NBI-6024) were prepared as described in Example 1. T cell antagonism was detected by evaluating the ability of the peptide analogues to inhibit T cell proliferation induced by native B chain (9–23) (SEQ ID NO:2). In this assay, antigen presenting cells were first irradiated and then incubated with the competing peptide analogue and the native B chain (9–23) peptide. T cells were then added to the culture. Various concentrations of candidate peptide analogues were included in cultures which were incubated for a total of 4 days. Following this incubation period, each culture was pulsed with 1 μCi of [$^3$H]-thymidine for an additional 12–18 hours. Cultures were then harvested on fiberglass filters and counted as above. Mean CPM and standard error of the mean were calculated from data determined in triplicate cultures. The results, shown in FIG. 2, indicate that the peptide analogues containing alanine substitutions at residue 12, 13 or 16 are capable of attenuating the response of the pathogenic insulin B chain (9–23) T cells.

Figure 3:
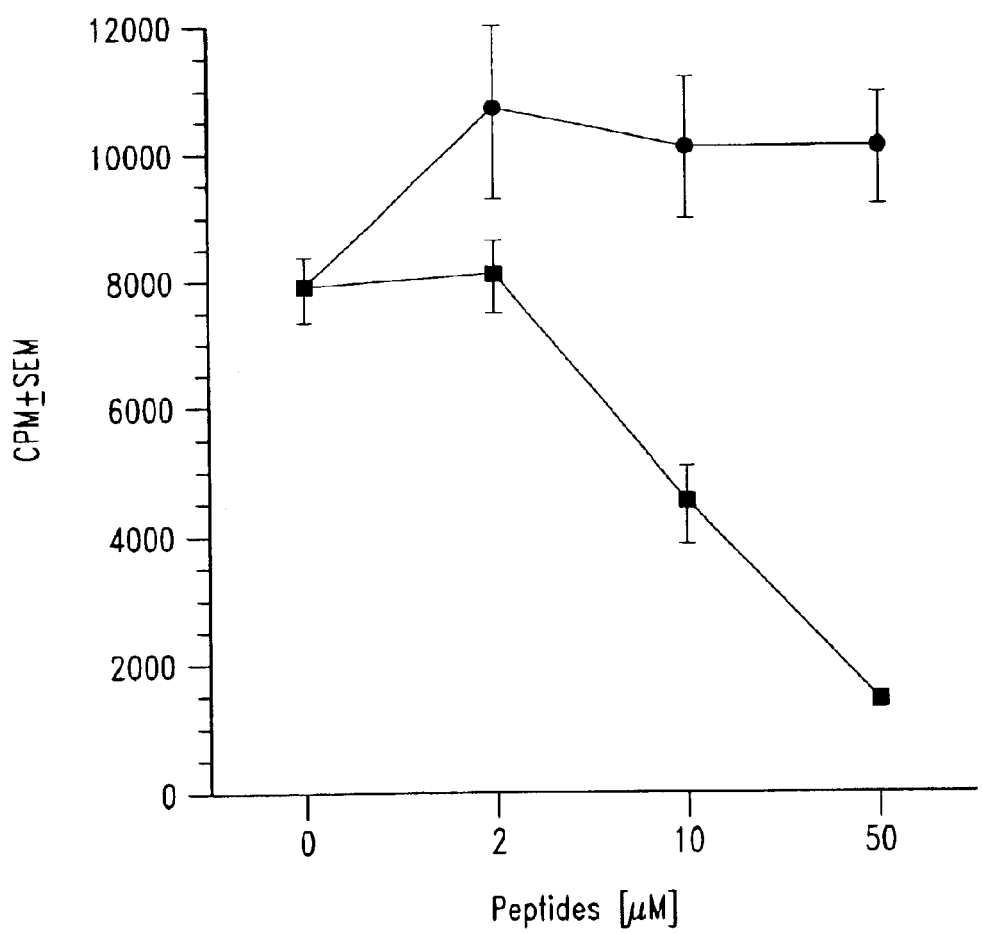
FIG. 3 is a graph showing the proliferative response (measured in cpm) of a NOD mouse T cell clone to a native insulin B chain (9–23) peptide in the presence of varying amounts of the representative peptide analogue in which amino acids at positions 16 and 19 are substituted with alanine (NBI-6024; indicated by squares). For comparison the proliferative response in the presence of an unrelated control peptide derived from myelin basic protein (NBI-5096; indicated by circles) is also shown. The response is shown as mean CPM±SEM of triplicate cultures.
Figure 4:
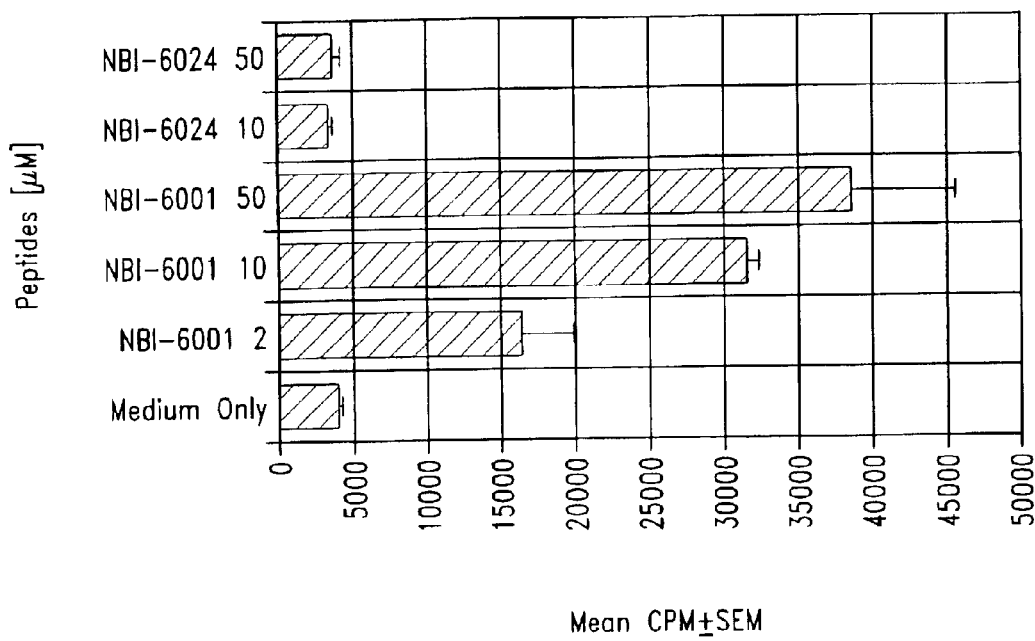
FIGS. 4–6 are histograms illustrating the proliferative response (measured in cpm) of T cell lines from different diabetic patients to the native B chain (9–23) peptide or to representative peptide analogues. Peripheral blood mononuclear cells were isolated from diabetic patients and cultured in the presence of insulin B chain (9–23) peptide. After three rounds of restimulation with insulin B chain (9–23), $1\times10^5$ T-cells and $7\times10^4$ irradiated autologous PBMCs were added to each well in a round bottom 96-well plate in complete medium. Cells were cultured for 5 days with NBI-6024 (insulin B chain 9–23 with alanine substitutions at positions 16 and 19), insulin B chain (9–23) or medium only. On day 4, the cells were pulsed with $^3$H-thymidine and re-cultured for an additional 18 hours. The cultures were then harvested, counted using liquid scintillation, and the data was expressed as the mean counts per minute (cpm) of replicate samples±standard error of the mean (sem).
Figure 5:
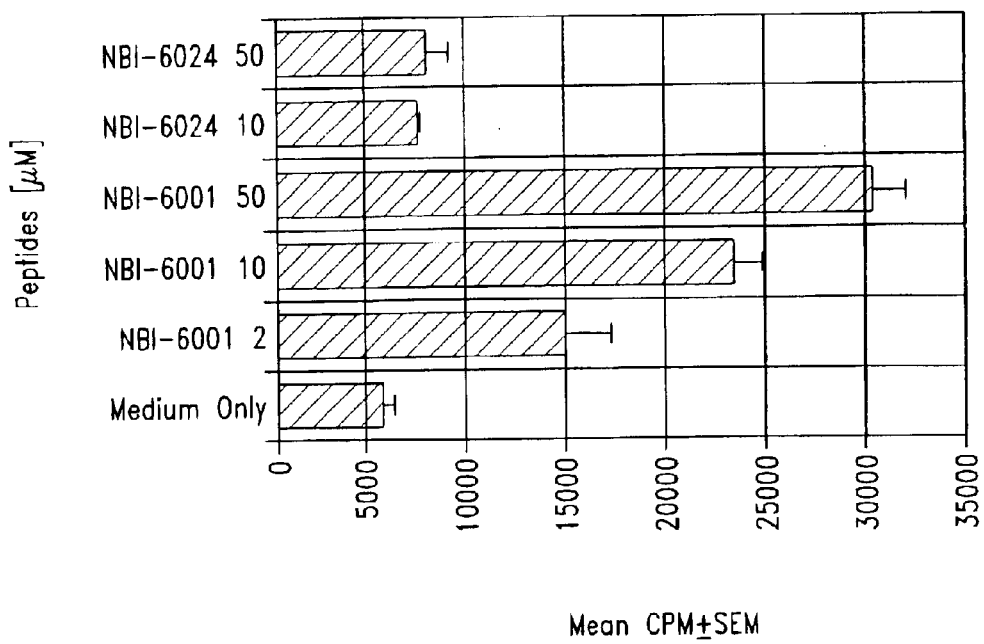
Figure 6:
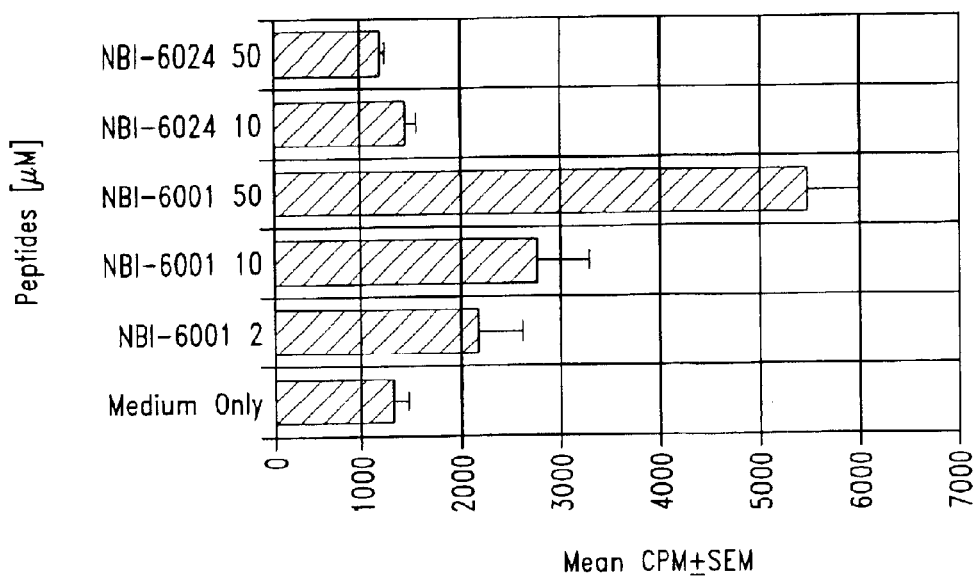
Figure 7:
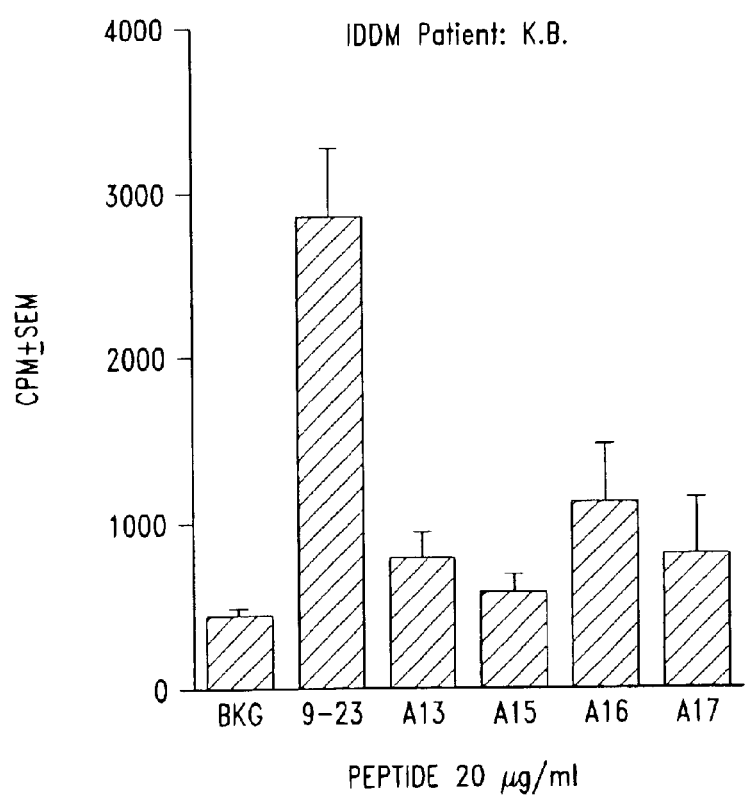
FIG. 7 is a histogram illustrating the proliferative response (measured in cpm) of a T cell line from a diabetic patient to the native B chain (9–23) peptide or to representative peptide analogues containing alanine substitutions as indicated. Peripheral blood mononuclear cells were isolated from diabetic patients and cultured in the presence of insulin B chain (9–23) peptide. After three rounds of restimulation with insulin B chain (9–23), $1\times10^5$ T-cells and $7\times10^4$ irradiated autologous PBMCs were added to each well in a round bottom 96-well plate in complete medium. Cells were cultured for 5 days with analogue, insulin B chain (9–23) or medium only (BKG), as indicated. On day 4, the cells were pulsed with $^3$H-thymidine and re-cultured for an additional 18 hours. The cultures were then harvested, counted using liquid scintillation, and the data was expressed as the mean counts per minute (cpm) of replicate samples±standard error of the mean (sem).

The ability of the doubly substituted peptide to inhibit insulin-dependent proliferation by T cells is shown in Table 4 and FIG. 3. Within Table 4, the control peptide, NBI-5096, is an unrelated peptide from myelin basic protein. The percent inhibition was calculated as: (1-experimental cpm/insulin peptide cpm)×100%.

TABLE 4

INHIBITION OF INSULIN B CHAIN (9–23) PEPTIDE RESPONSE IN TWO MURINE NOD T CELL CLONES BY A PEPTIDE ANALOGUE

| Clone | Conditions | CPM ± SEM | % Inhibition |
|---|---|---|---|
| PD12-2.35 | Medium Only | 213 ± 17 | |
| | B(9–23) 5 μM | 7,840 ± 528 | |
| | B(9–23) 5 μM + 10 μM NBI-6024 | 4,441 ± 626 | 43.0 |
| | B(9–23) 5 μM + 50 μM NBI-6024 | 1,389 ± 218 | 82.0 |
| | B(9–23) 5 μM + 10 μM NBI-5096 | 10,089 ± 1,113 | N/A |
| | B(9–23) 5 μM + 50 μM NBI-5096 | 10,125 ± 887 | N/A |
| PD12-2.40 | Medium Only | 305 ± 13 | |
| | B(9–23) 5 μM | 9,149 ± 1,062 | |
| | B(9–23) 5 μM + 10 μM NBI-6024 | 6,379 ± 1,485 | 30.0 |
| | B(9–23) 5 μM + 50 μM NBI-6024 | 4,305 ± 941 | 52.9 |
| | B(9–23) 5 μM + 10 μM NBI-5096 | 12,336 ± 1,556 | N/A |
| | B(9–23) 5 μM + 50 μM NBI-5096 | 17,988 ± 584 | N/A |

N/A = Not applicable as no inhibition was observed.

The ability of NBI-6024 to block the B chain (9–23) peptide-induced stimulation of NOD derived T clones suggests that the alterations at positions 16 and 19 of the native insulin B chain (9–23) peptide did not alter the ability of the analogue to be recognized by the pathogenic T cells. Moreover, these results indicate that the analogue also binds to the MHC with sufficient affinity to allow for recognition by the insulin B chain (9–23)-specific T cell.

EXAMPLE 5

Effect of Peptide Analogues on Proliferation of T Cell Lines and Clones from Diabetic Patients This Example illustrates the lack of stimulation of T cell lines and clones derived from diabetic patients by representative peptide analogues.

Peptide analogues of B chain (9–23) containing alanine substitutions at residues 13, 15, 16 or 17 or the doubly substituted alanine analog A$^{16, 19}$ (NBI-6024) were prepared as described in Example 1. T cell lines from diabetic patients were prepared by isolating lymphocytes from the blood of the patient by subjecting the blood to a density gradient separation. Isolated lymphocytes were then cultured in the presence of the insulin B chain (9–23) peptide (10 μM) and recombinant human IL-2 in the presence of 5–10% of autologous serum and irradiated autologous peripheral blood lymphocytes in culture medium. Four to five days later cells were harvested and the cycle repeated for 2 or 3 times.

Proliferation of the T cell line, in response to the native B chain (9–23) peptide (SEQ ID NO:2) or to the peptide analogs, was measured by culturing 25,000 to 100,000 T cells in the presence of 50,000–200,000 irradiated autologous PBLs and different concentrations of the insulin B chain (9–23) peptide or a peptide analogue in triplicate cultures. Following 4–5 days of culture, including the last 18 hours with radioactive thymidine, cells were harvested and the associated radioactivity was counted in a liquid scintillation counter. Results are expressed as mean counts per minute for each of the peptide analogues tested.

The results, shown in FIGS. 4–7, indicate that T cell lines and clones that proliferate in response to the native insulin B chain (9–23) peptide (SEQ ID NO:2) are not stimulated by the peptide analogues. The results from these patients and others are summarized in Table 5.

TABLE 5

PROLIFERATIVE RESPONSE OF PATIENT PBLS TO NATIVE INSULIN PEPTIDE OR THE ANALOGUE NBI-6024

| | | Stimulation Index* | |
|---|---|---|---|
| Patient Number | Patient ID | Insulin B (9–23) [50 μM] | NBI-6024 [50 μM] |
| 1 | 100 | 9.9 | 0.9 |
| 2 | 200 | 5.3 | 1.2 |
| 3 | 400 | 7.8 | 1.0 |
| 4 | 500 | 2.1 | 0.9 |
| 5 | 600 | 5.8 | 1.6 |
| 6 | 700 | 3.2 | 1.5 |
| 7 | 900 | 2.6 | 0.9 |
| 8 | 1100 | 3.7 | 0.8 |

*Stimulation Index = CPM with antigen/CPM with medium alone (no antigen)

The results clearly demonstrate that cells from diabetic patients that are responsive to the insulin B chain (9–23) peptide do not respond to the altered peptide ligand, NBI-6024 which has substitutions at position 16 and 19. We have also determined that the APL NBI-6024 binds with similar affinity to DQ8 antigens. Thus, the absence of stimulation of the diabetic patient's T cells by NBI-6024 is not due to any incompatibility of the peptide with the presenting MHC molecules, but is more likely due to altered recognition by the B chain (9–23)-specific T cells.

EXAMPLE 6

Reduction of Incidence of Diabetes in NOD Mice

This Example illustrates the ability of representative peptide analogs to prevent diabetes in NOD mice.

The NOD mouse spontaneously develops diabetes beginning around 3 months of age (Makino et al., in Current Topics in Clinical and Experimental Aspects of Diabetes Mellitus, Sakamoto et al., eds., p. 25–32 (Elsevier, Amsterdam, 1985)). The disease is preceded by cellular infiltration into the pancreas of T cells beginning even by one month of age. Soluble peptide analogues of B chain (9–23) containing alanine substitutions at residues 12, 13 or 16 were administered subcutaneously to NOD mice at weekly intervals. 400 μg of each peptide were administered at each treatment to ten animals. Following 9 treatments, the percent of mice in each treatment group that had become diabetic was evaluated by measuring blood glucose levels using a glucometer at weekly intervals. A reading of more than 200 mg/dl of blood glucose on two consecutive observations was considered indicative of frank diabetes.

Figure 8:
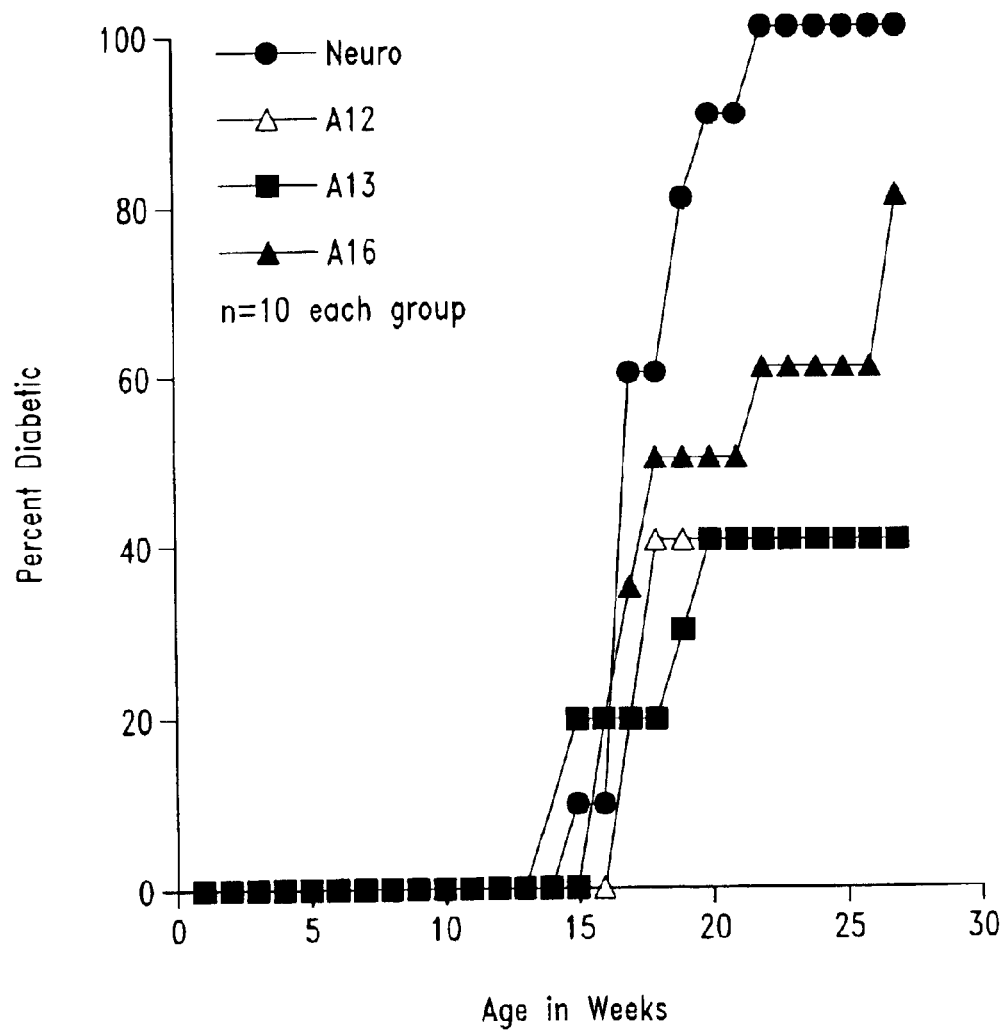
FIG. 8 is a graph showing the percent of female NOD mice that were diabetic following nine weekly treatments with representative peptide analogues. Ten mice each were treated subcutaneously beginning on day 24 with peptide analogues of the B chain (9–23) containing alanine substitutions at residue 12 (open triangles), 13 (squares) or 16 (solid triangles). All of the mice treated with a control peptide, neurotensin (circles), became diabetic.
Figure 9:
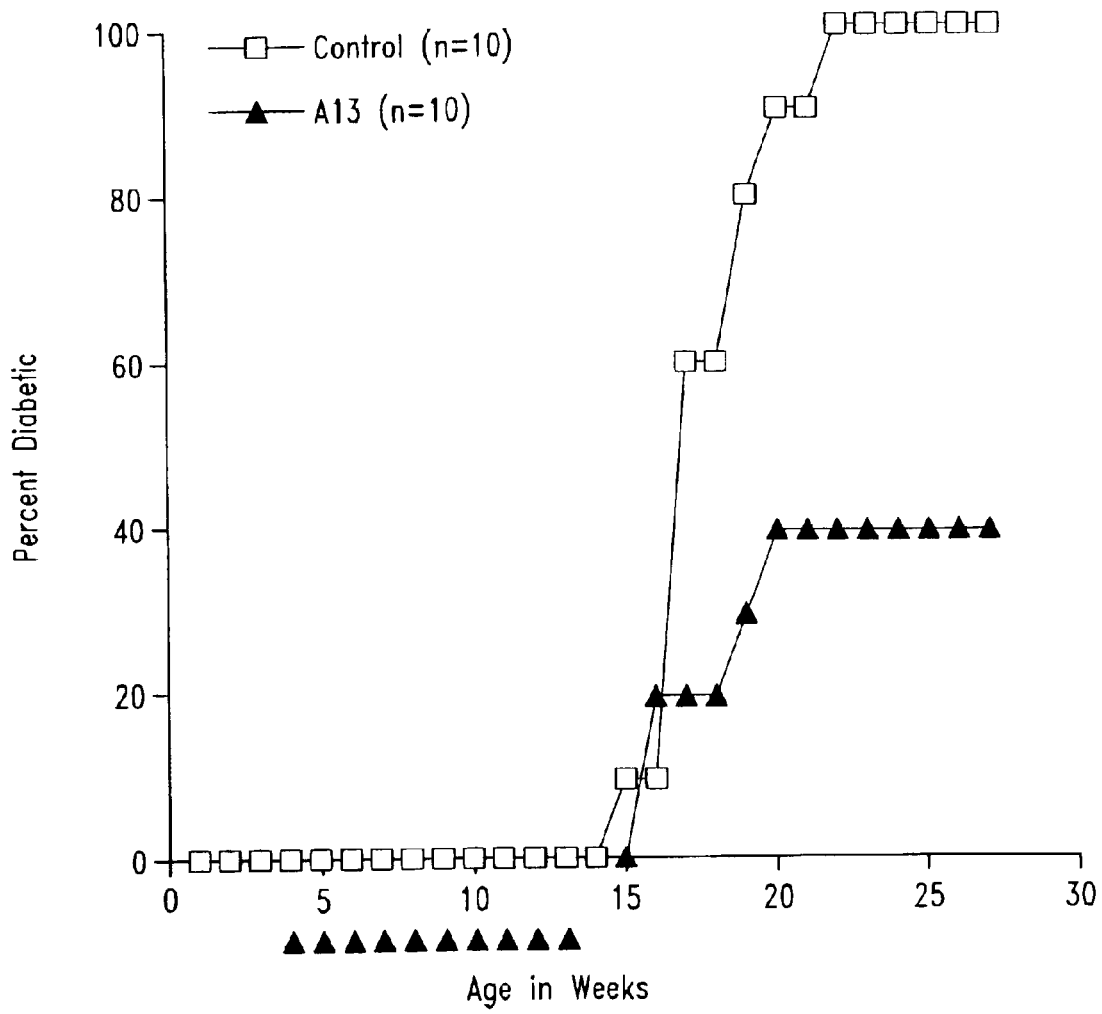
FIG. 9 is a graph showing the same data as in FIG. 8, but contrasting only the A13 analogue-treated group with the control peptide (neurotensin)-treated group.

As shown in FIG. 8, treatment with each of the alanine-substituted analogues resulted in a marked reduction in the incidence of diabetes. The data for the A13 substituted analogue is also shown in FIG. 9.

Figure 10:
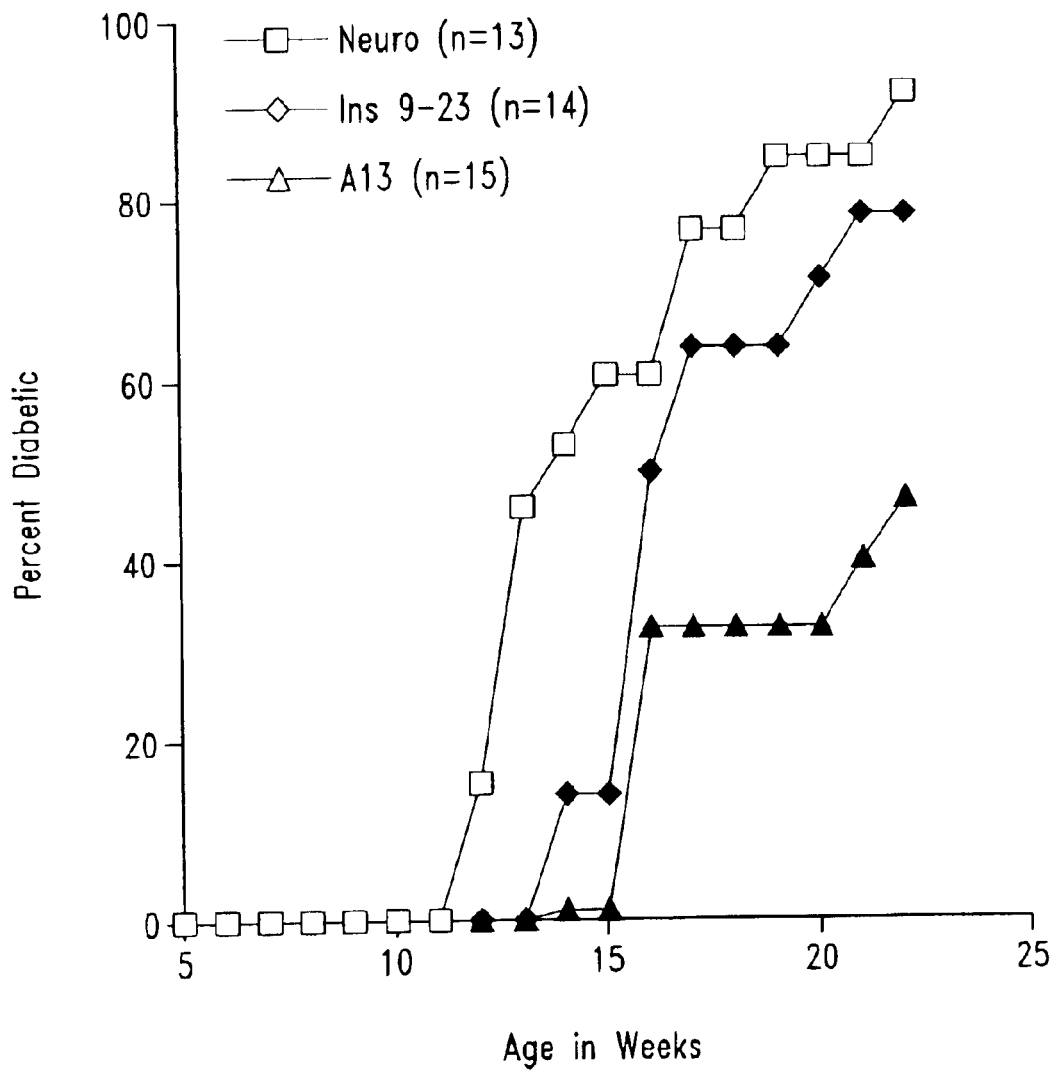
FIG. 10 is a graph showing the percent of NOD mice that were diabetic following 13 weekly treatments with a representative peptide analogue. Ten mice were treated subcutaneously beginning on day 24 with 400 μg of neurotensin (squares), B chain (9–23) {diamonds} or a peptide analogue of the B chain (9–23) containing an alanine substitution at residue 13 (triangles).

In another experiment, B chain (9–23), the A13 substituted analogue or neurotensin (as a control) was administered subcutaneously to NOD mice at weekly intervals. 400 μg of each peptide were administered at each treatment to ten animals. Following 13 treatments, the percent of mice in each treatment group that had become diabetic was evaluated as described above. As shown in FIG. 10, the B chain (9–23) peptide reduced the incidence of diabetes. This reduction was more pronounced for the A13 substituted analogue.

Figure 11:
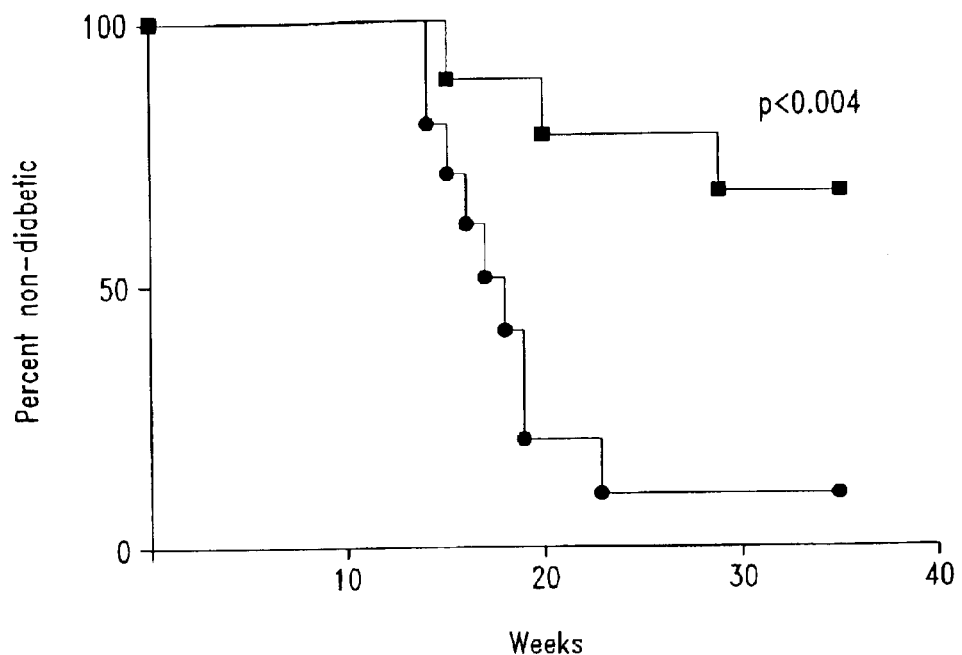
FIG. 11 is a graph showing the effect of representative peptide analogues on the incidence of diabetes in NOD mice. Four week old female NOD mice (n=9) were treated subcutaneously with 20 mg/kg of NBI-6024 ($A^{16,19}$) at weekly intervals for 12 weeks, followed by every other week until 35 weeks of age. The control group (n=10) consisted of untreated animals. Mice with blood glucose greater than 200 mg/dL at two consecutive time points were considered to be diabetic. The data are expressed as the percent of non-diabetic over the 35-week study. The log-rank test was used to assess whether the results of the two treatment groups were significantly different. The percent of NOD mice that were diabetic following treatments with NBI-6024 ($A^{16,19}$) is indicated at the various time points by squares, and the percent of mice that were diabetic in the control group is indicated by circles.

To determine the ability of the double substituted peptide $A^{16,19}$ (NBI-6024) to control the development of diabetes in the NOD mice, the peptide was administered to animals at an early age. Thus, female mice (n=9, approximately 4 weeks old) were treated subcutaneously with 20 mg/kg (400 μg/mouse) of NBI-6024 for twelve weeks and then every other week until Week 35. Beginning at 9–10 weeks of age, mice were then monitored weekly for hyperglycemia, measuring the blood glucose levels. As a control, a group of 10 female mice was left untreated. The results from this experiment are shown in FIG. 11. As can be seen, treatment with NBI-6024 significantly reduced the incidence of diabetes by about 60–70%, compared to the untreated group, (p<0.004).

Figure 12:
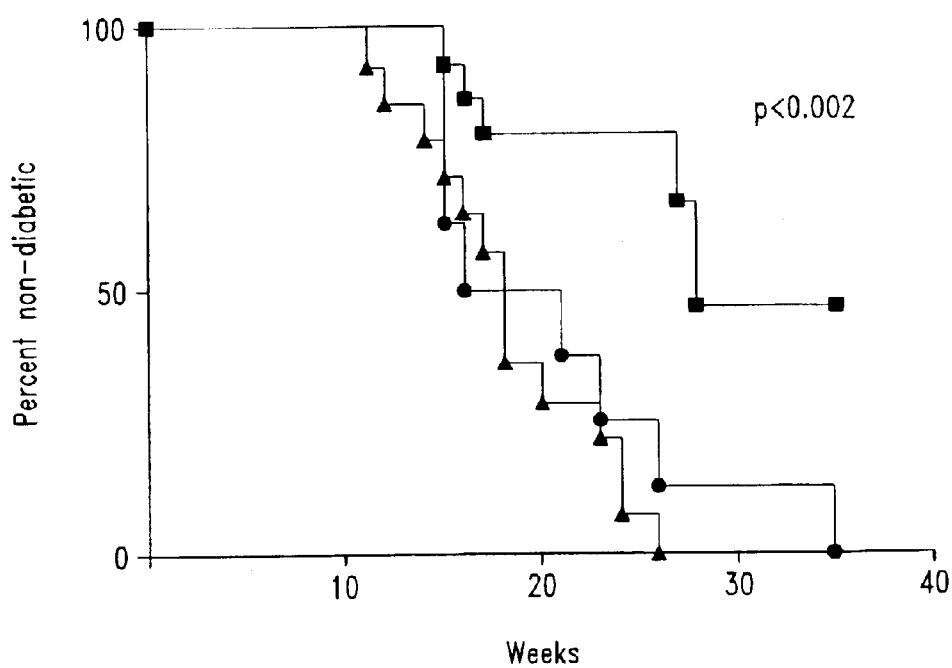
FIG. 12 is a graph showing the effect of representative peptide analogues on the incidence of diabetes in NOD mice. Four week old female NOD mice (n=13–15) were treated subcutaneously with 20 mg/kg of NBI-6024 ($A^{16,19}$) or NBI-6201 (a control peptide, neurotensin) at weekly intervals for 12 weeks, followed by every other week until 35 weeks of age. An additional control group (n=8) consisted of untreated animals. Mice with blood glucose greater than 200 mg/dL at two consecutive time points were considered to be diabetic. The data are expressed as the percent of non-diabetic over the 35-week study. The log-rank test was used to assess whether the results of the two treatment groups were significantly different. The percent of NOD mice that were diabetic following treatments with NBI-6024 ($A^{16,19}$) is indicated at the various time points by squares, the percent that were diabetic following treatment with the neurotensin peptide is shown by triangles, and the percent of untreated mice that were diabetic is indicated by circles.
Figure 13A:
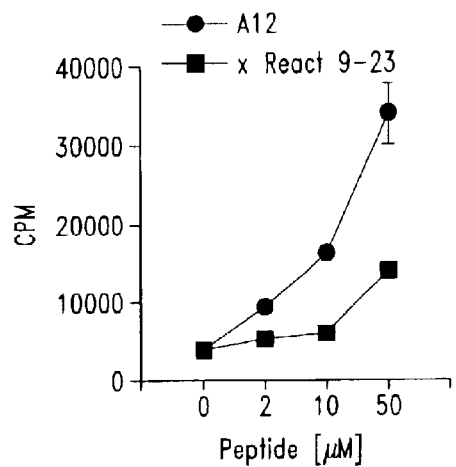
FIGS. 13A–13D are graphs illustrating the immunogenicity of representative peptide analogues containing B chain residues 9–23 with an alanine substitution at residue 12 (FIG. 13A), residue 13 (FIG. 13B), residue 15 (FIG. 13C) or residue 16 (FIG. 13D). NOD mice were injected 2–4 times subcutaneously with the peptide analogue in soluble form before assaying the proliferative response of lymph node cells to varying concentrations of either the peptide analogue or native insulin B chain (9–23) peptide as indicated. Proliferative response was assessed by determining the amount of radioactive thymidine incorporated in the cells (plotted as mean counts per minute (CPM) of triplicate culture wells) by counting in a liquid scintillation counter following completion of the culture period.
Figure 13B:
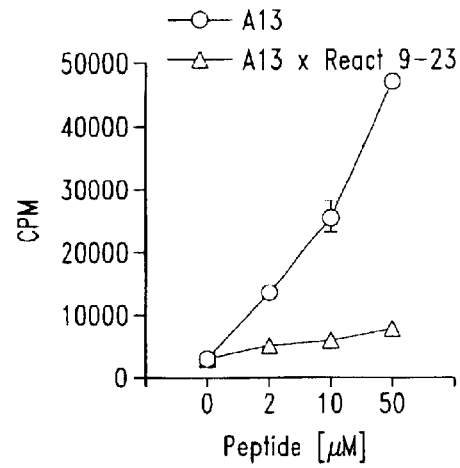
Figure 13C:
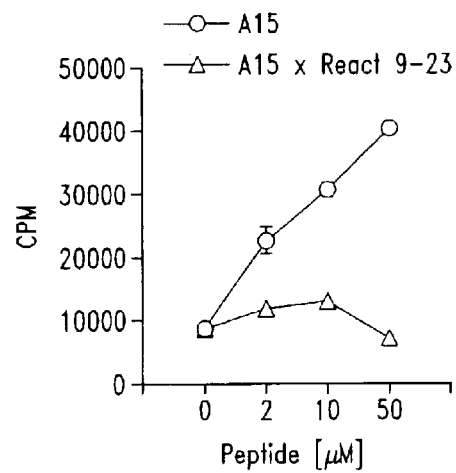
Figure 13D:
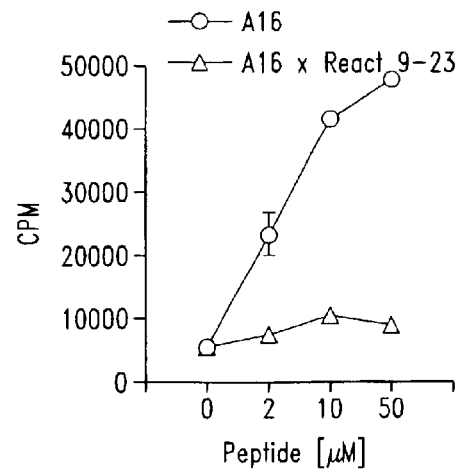
Figure 14A:
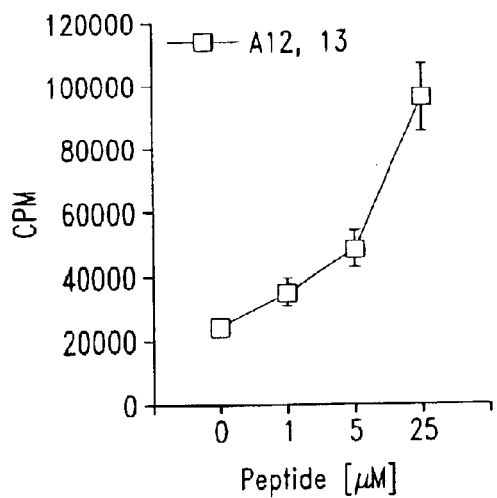
FIGS. 14A–14F are graphs showing the immunogenicity of six different peptide analogues in the NOD mice. Peptide analogues with two alanine substitutions (A12,13; A12,15; A12,16; A13,15; A13,16 and A15,16, as indicated) were injected in NOD mice and after 10 days their lymph node cells were used in a proliferation assay using different concentrations of the immunizing peptide as stimulators. Proliferative response was assessed by determining the amount of radioactive thymidine incorporated in the cells (plotted as mean counts per minute (CPM) of triplicate culture wells) by counting in a liquid scintillation counter following completion of the culture period.
Figure 14B:
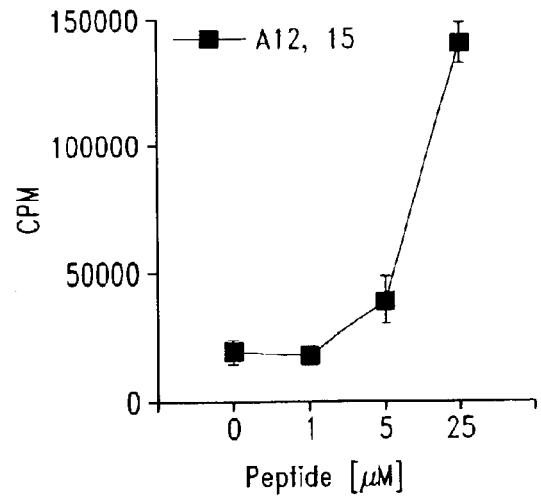
Figure 14C:
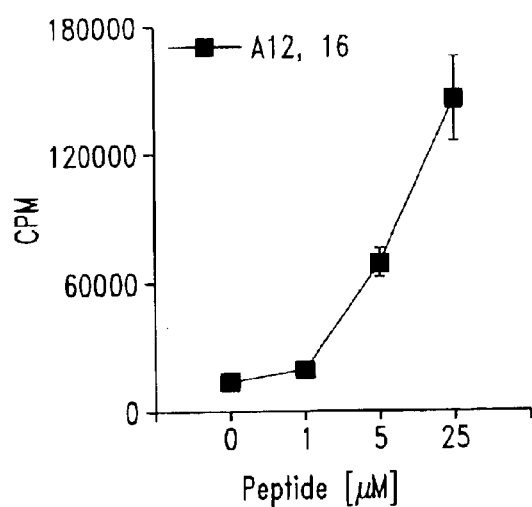
Figure 14D:
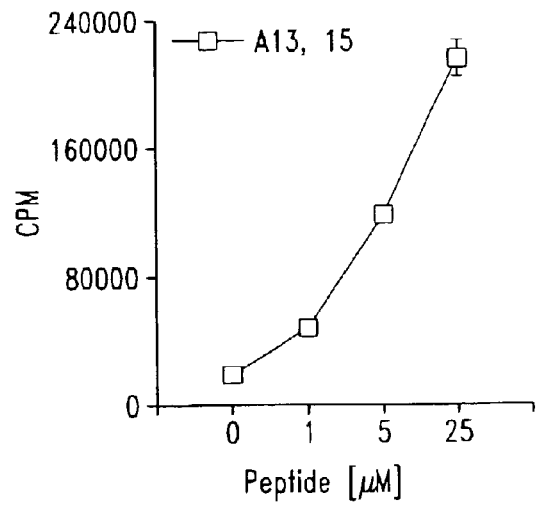
Figure 14E:
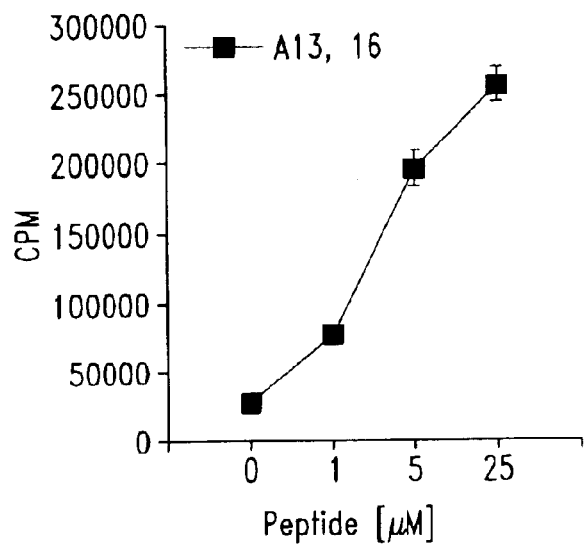
Figure 14F:
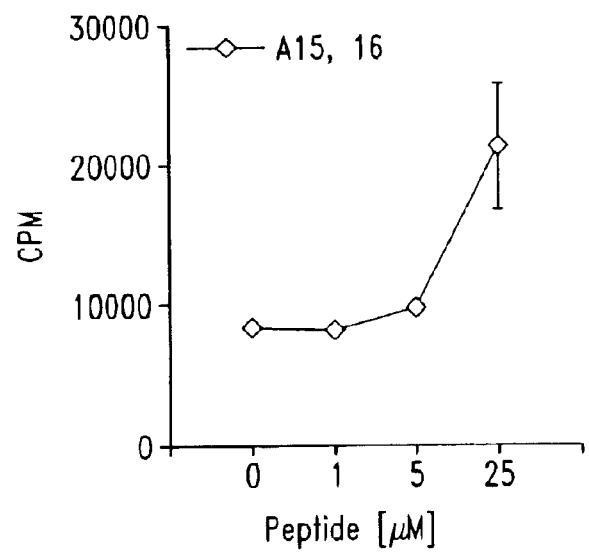
Figure 15A:
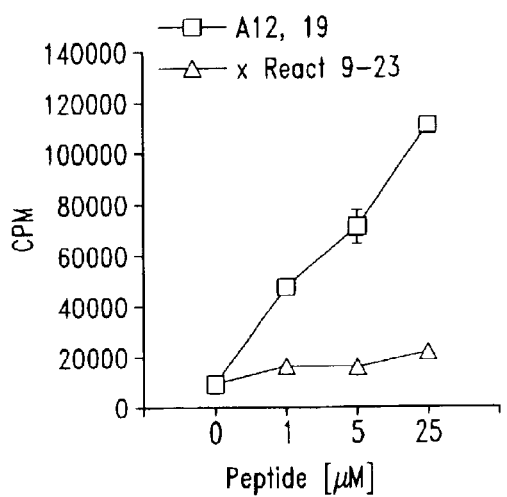
FIGS. 15A–15D are graphs illustrating the immunogenicity of representative double substituted peptide analogs of insulin B chain (9–23). The following peptides were tested for their ability to elicit an immune response in NOD mice: A12,19 (FIG. 15A); A13,19 (FIG. 15B); A15,19 (FIG. 15C); A16,19 (FIG. 15D). Proliferative response as counts per minute of the draining lymph node cells is shown in response to the immunizing analogue and also to the native insulin B chain (9–23) peptide.
Figure 15B:
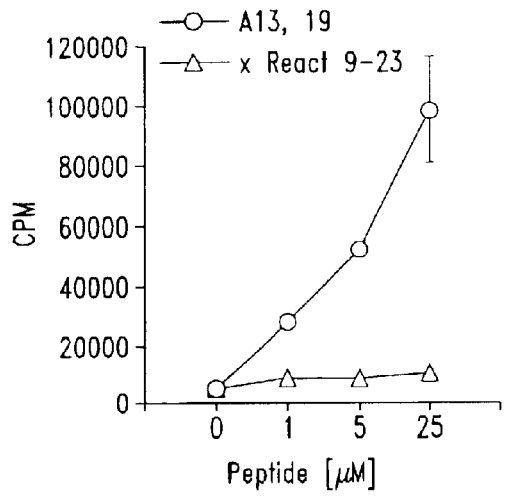
Figure 15C:
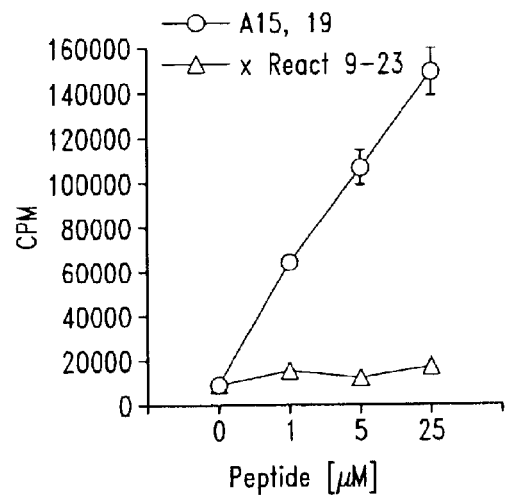
Figure 15D:
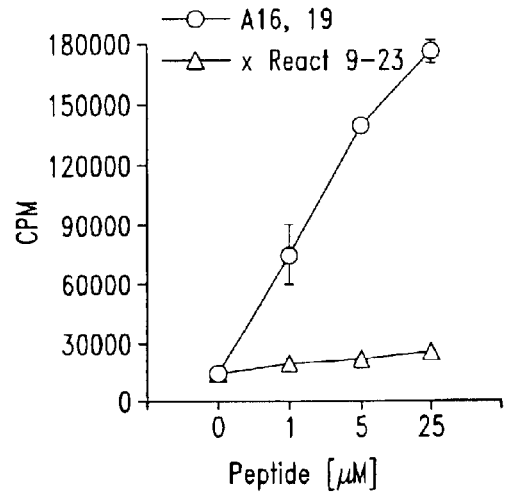
Figure 16:
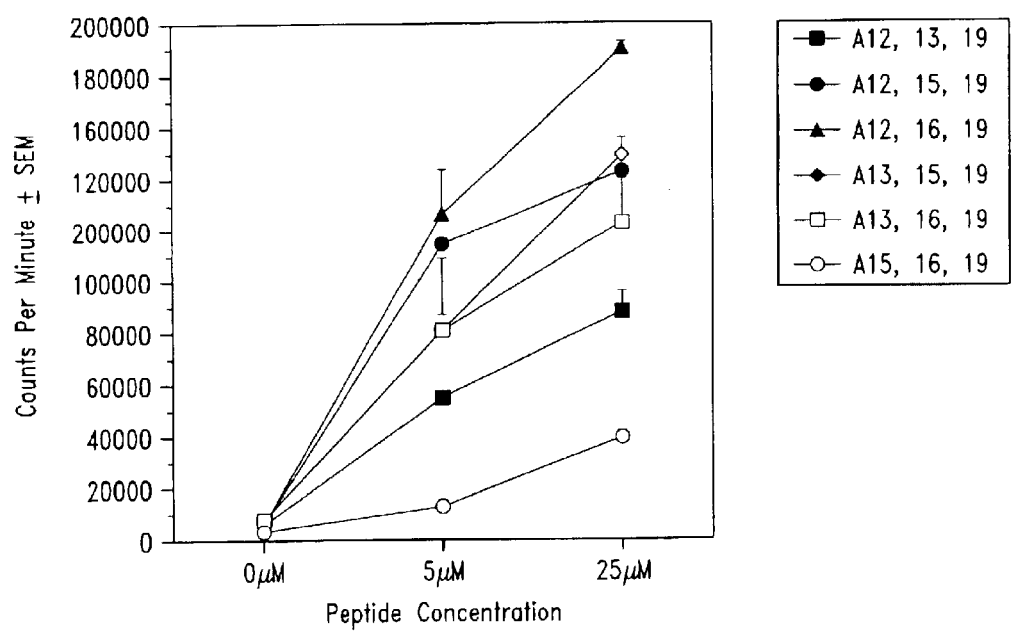
FIG. 16 is a graph showing the ability of a series of triple substituted peptides to evoke a T cell proliferative response in NOD mice. Mice were immunized separately with representative peptide analogues containing the following combinations of substitutions: A12,13,19; A12,15,19; A12,16,19; A13,15,19; or A13,16,19; A15,16,19. Lymph node cells were then used in a proliferation assay, and the response to each of the immunizing peptides at different concentrations is shown.

The observations were then confirmed and extended in a second experiment. Here, animals (n=13–15) were treated with either NBI-6024 or an unrelated peptide, neurotensin, NBI-6201 as described above. An additional group (n=8) was left untreated. As shown in FIG. 12, treatment with 20 mg/kg of the altered peptide NBI-6024 resulted in a reduced incidence of diabetes compared to either the neurotensin treated or untreated group.

These results demonstrate that the altered peptide ligand NBI-6024, designed around insulin B chain (9–23) peptide was capable of conferring protection to animals at risk to develop diabetes spontaneously. It is likely that T cells that recognize other pancreas antigens are present in these animals, yet they too appear to be regulated by the insulin APL. The timing of administration was approximately at the same time that autoreactive lymphocytes begin to infiltrate the pancreas and initiate the destructive process. These results offer hope that early intervention with this APL may prove useful in delaying or preventing the onset of Type I diabetes in people.

EXAMPLE 7

Immunogenicity of Representative Peptide Analogues

This Example illustrates the immunogenicity of representative peptide analogues in NOD mice.

Groups of 3–4 NOD mice were immunized with 100–400 μg of peptide analogues subcutaneously in mannitol acetate buffer three times within a period of 10–15 days. Following the last immunization, lymph node cells and/or spleen cells were used in a proliferation assay in which different concentrations of the immunizing peptide were cultured with the cells for 3–4 days. The last 18 hours of culture included tritiated thymidine. Cells were harvested and counted in a scintillation counter and the response is expressed as CPM±SEM. These results, shown in FIGS. 13–16, indicate that these representative peptide analogues have the ability to bind to the mouse MHC molecules and be recognized by the corresponding T cells.

The ability of the double substituted peptide NBI-6024 ($A^{16,19}$) to induce a cellular immune response in NOD mouse strain was next determined. Two female NOD mice were immunized with 10 mg/kg NBI-6024 either as an aqueous suspension or, as a control, emulsified in complete Freund's adjuvant (CFA). On Day 8, three days following the last injection, the mice were sacrificed, the spleen and inguinal lymph node cells were removed and pooled, and a single-cell suspension was prepared. Cells were cultured in the presence of varying concentrations (0–25 μM) of NBI-6024. The ability of these lymphoid cells to proliferate in response to NBI-6024 was measured in vitro by [$^3$H]-thymidine incorporation.

The results are presented in Table 6, in which the response is expressed as mean CPM±SEM of triplicate cultures. Lymph node cells isolated from mice immunized with the analogue in CFA showed a strong proliferative response to challenge with the immunizing analogue in a dose-dependent manner (Table 6). These results indicate that alterations made in the native insulin B chain (9–23) sequence at positions 16 and 19 have not affected the ability of the peptide to bind the NOD disease-associated MHC haplotype molecule and, more importantly, did not hinder recognition by T cells.

TABLE 6

PROLIFERATIVE RESPONSE OF LYMPH NODE CELLS TO NBI-6024 FROM NOD MICE IMMUNIZED WITH NBI-6024 IN CFA

| NBI-6024 (μM) | Proliferative Response (CPM ± SEM) |
| --- | --- |
| 0 | 2,445 ± 137 |
| 1 | 140,061 ± 7,289 |
| 5 | 187,711 ± 2,548 |
| 25 | 218,149 ± 4,462 |

Figure 17A:
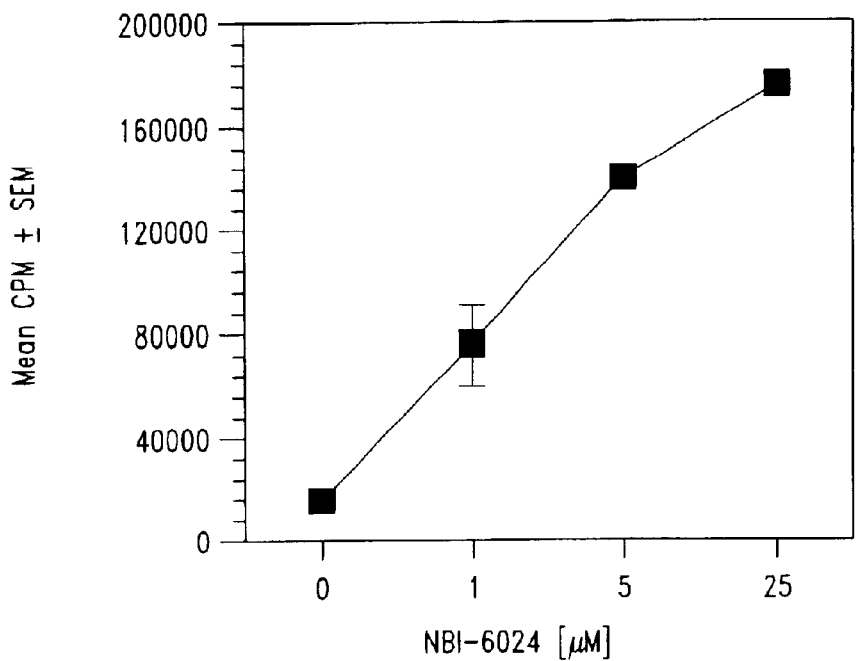
FIGS. 17A and 17B are graphs showing the ability of a double substituted peptide ($A^{16,19}$) to evoke an immune response. Five female NOD mice were immunized subcutaneously with 20 mg/kg of soluble NBI-6024 on days 1, 6 and 12. On day 15, the mice were sacrificed, the inguinal lymph node cells removed and cultured in the presence of varying concentrations (0–50 μM) of either NBI-6024 (FIG. 17A) or insulin B chain (9–23) peptide (FIG. 17B). The extent of T-cell proliferation was determined using $^3$H-thymidine incorporation. The response is expressed as mean CPM±SEM of triplicate cultures.
Figure 17B:
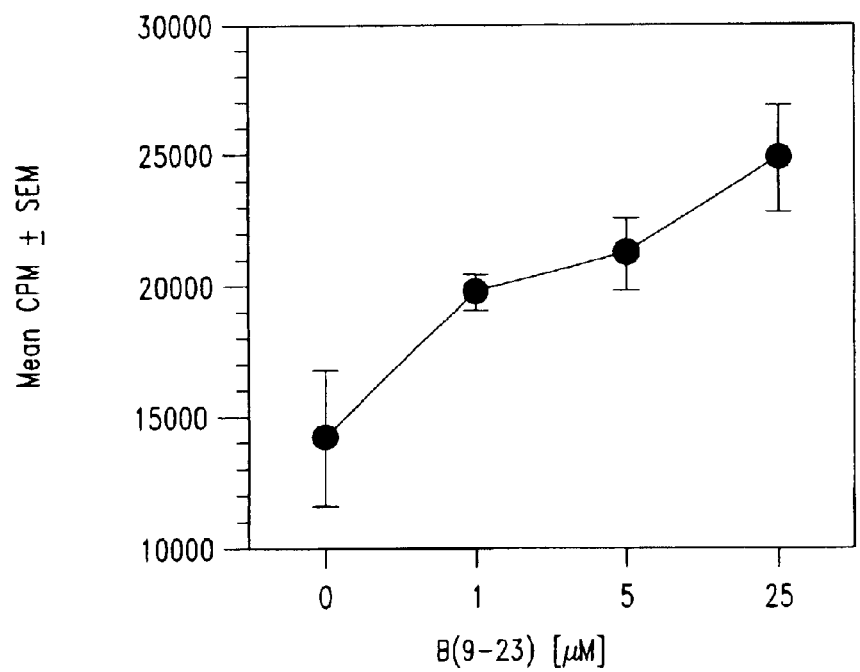

In addition, both the spleen and inguinal lymph nodes cells isolated from soluble administrated peptide exhibited a strong proliferative response to the APL when challenged in vitro with NBI-6024 (Table 7 and FIGS. 17A and 17B). Even more impressive was the finding that NBI-6024-derived lymphocytes from mice immunized with the soluble peptide also responded to Insulin B chain (9–23). This cross-reactive feature was not seen with CFA-emulsified peptide. This ability of the soluble peptide to induce a cross-reactive response may be desirable in controlling diabetes, as it may help to mobilize the protective NBI-6024-specific T cells to the pathogenic target tissue.

TABLE 7

PROLIFERATIVE RESPONSE TO NBI-6024 OR NATIVE INSULIN B-CHAIN (9–23) OF T CELLS FROM NOD MICE IMMUNIZED WITH SOLUBLE NBI-6024

| NBI-6024 Induced T Cell Line | Peptide Conc. [μM] | CPM ± SEM NBI-6024 | CPM ± SEM Insulin B(9–23) |
| --- | --- | --- | --- |
| Mouse # 1 | 0 | 19,130 ± 2191 | 19,130 ± 2191 |
| | 1 | 48,319 ± 1918 | 16,870 ± 4469 |
| | 5 | 160,673 ± 2269 | 21,292 ± 3216 |
| | 25 | 268,005 ± 11198 | 33,317 ± 3619 |

TABLE 7-continued

PROLIFERATIVE RESPONSE TO NBI-6024 OR NATIVE INSULIN
B-CHAIN (9–23) OF T CELLS FROM NOD MICE IMMUNIZED
WITH SOLUBLE NBI-6024

| NBI-6024 Induced T Cell Line | Peptide Conc. [μM] | CPM ± SEM NBI-6024 | CPM ± SEM Insulin B(9–23) |
|---|---|---|---|
| Mouse # 2 | 0 | 21,588 ± 2326 | 21,588 ± 2326 |
| | 1 | 54,519 ± 5666 | 17,262 ± 602 |
| | 5 | 126,123 ± 13851 | 19,648 ± 2169 |
| | 25 | 202,707 ± 8125 | 30,612 ± 3557 |
| Mouse # 3 | 0 | 24,006 ± 2803 | 24,006 ± 2803 |
| | 1 | 64,239 ± 9493 | 25,825 ± 3841 |
| | 5 | 140,836 ± 11778 | 58,567 ± 2737 |
| | 25 | 240,278 ± 15015 | 113,366 ± 515 |

Figure 18:
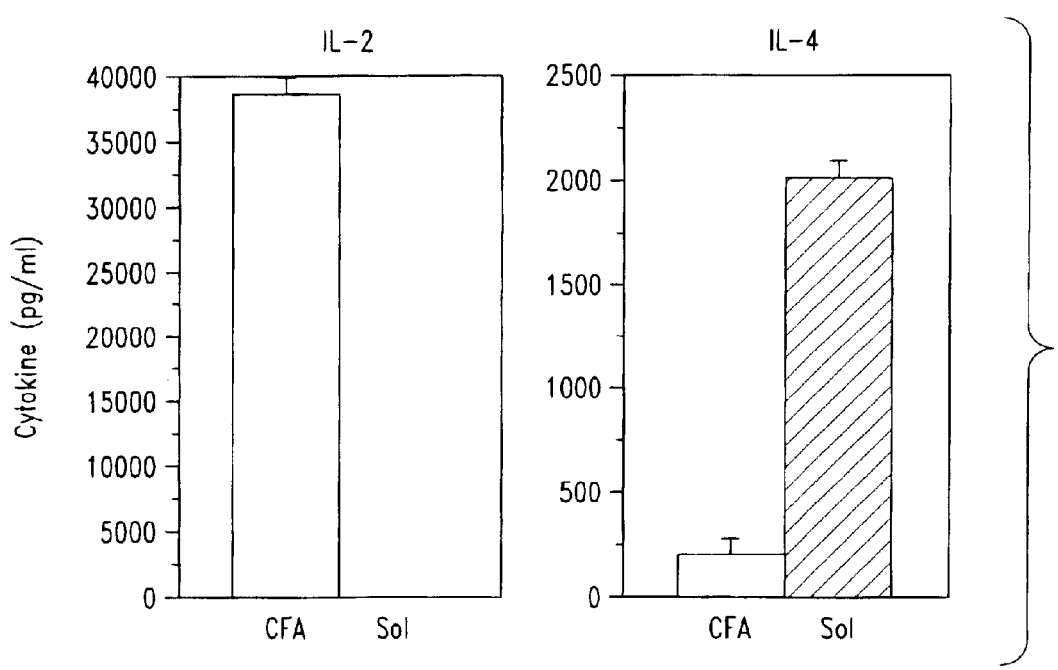
FIG. 18 is a histogram showing a comparison of the cytokines produced by immune cells induced by $A^{16,19}$ (NBI-6024) peptide in the presence or absence of adjuvant. Groups of NOD mice were immunized with the NBI-6024 alone or emulsified with CFA. The cytokines IL-2 and IL-4, as indicated, were measured at 25 μM of NBI-6024 and expressed as pg/mL after subtracting the background values.

To determine the type of T cells produced following soluble administration of NBI-6024, the culture supernatants from immune lymphoid cells were removed 48 hours following the initiation of culture and the levels of various cytokines measured using stantard ELISA technology. Strikingly, the cytokine production profile of the T cells mice immunized with soluble NBI-6024 produced the Th2 cytokines, interleukin-4 (FIG. 18) and interleukin-5 (Table 8), and not the Th1-derived interleukin-2. Within Table 8, values are expressed in pg/ml as mean of triplicates±SEM. As a control, NBI-6024 emulsified with CFA did induce the expected Th1-cytokine profile (IL-2) from immune T cells upon in vitro stimulation.

TABLE 8

CYTOKINE RESPONSE OF SOLUBLE NBI-6024 INDUCED T CELLS
CULTURED WITH NBI-6024

| NBI-6024 [mM] | Cytokine (pg/ml) | | |
|---|---|---|---|
| | IL-2 | IL-4 | IL-5 |
| 0 | <15 pg/ml | 134 ± 0 | 1,814 ± 332 |
| 1 | <15 pg/ml | 684 ± 92 | 9,999 ± 503 |
| 5 | <15 pg/ml | 1,653 ± 51 | 23,496 ± 684 |
| 25 | <15 pg/ml | 2,102 ± 85 | 28,062 ± 141 |

The ability of the soluble subcutaneous administration of NBI-6024 to induce Th2-like cells is a desirable feature, as such cells are associated with recovery from diabetes and other organ-specific autoimmune diseases (Sarvetnick, *J. Exp. Med.* 184: 1597–1600, 1996; Shaw et al., 1997; Balasa et al., *J. Exp. Med.* 186: 385–391, 1997). These Th2-derived cytokines have strong anti-inflammatory activities that suppress development of pro-inflammatory cytokine-secreting auto-reactive Th1 cells that mediate disease.

From the foregoing, it will be evident that although specific embodiments of the invention have been described herein for the purpose of illustrating the invention, various modifications may be made without deviating from the spirit and scope of the invention. Accordingly, the present invention is not limited except as by the appended claims.

What is claimed is:

1. A peptide analogue comprising residues 9 to 23 of human insulin B chain of SEQ ID NO:1, wherein the peptide analogue differs in sequence from native human insulin B chain residues 9 to 23 due to amino acid substitutions at between 1 and 4 amino acid positions, wherein at least one substitution occurs at a residue selected from the group consisting of residues 12, 13, 15 and 16, wherein the peptide analogue is capable of reducing incidence of diabetes in non-obese diabetic (NOD) mice, and wherein the peptide analogue consists of no more than 18 residues of human insulin B chain.

2. The peptide analogue of claim 1, wherein the peptide analogue has a sequence that differs from native human insulin B chain at two amino acid residues.

3. The peptide analogue of claim 1, wherein the peptide analogue has a sequence that differs from native human insulin B chain at three amino acid residues.

4. The peptide analogue of claim 1, wherein an amino acid substitution occurs at residue 19.

5. The peptide analogue of claim 1, wherein at least one amino acid substitution is non-conservative.

6. The peptide analogue of claim 1, wherein residue 12 is substituted.

7. The peptide analogue of claim 6, wherein residue 12 is an alanine residue.

8. The peptide analogue of claim 1, wherein residue 13 is substituted.

9. The peptide analogue of claim 8, wherein residue 13 is an alanine residue.

10. The peptide analogue of claim 1, wherein residue 15 is substituted.

11. The peptide analogue of claim 10, wherein residue 15 is an alanine residue.

12. The peptide analogue of claim 1, wherein residue 16 is substituted.

13. The peptide analogue of claim 12, wherein residue 16 is an alanine residue.

14. The peptide analogue of claim 1, wherein residue 19 is substituted and wherein a residue selected from the group consisting of residues 12, 13, 15 and 16 is an alanine residue.

15. The peptide analogue of claim 14, wherein residue 19 is an alanine residue.

16. The peptide analogue of claim 1, further comprising residue 24 of human insulin B chain.

17. The peptide analogue of claim 1, wherein the peptide analogue comprises no more than 16 residues of human insulin B chain.

18. The peptide analogue of claim 1, wherein the peptide analogue comprises no more than 15 residues of human insulin B chain.

19. A pharmaceutical composition comprising a peptide analogue according to any one of claims 1–16, 17 and 18 in combination with a physiologically acceptable carrier or diluent.

20. A peptide analogue comprising residues 9 to 23 of human insulin B chain of SEQ ID NO:1, wherein the peptide analogue differs in sequence from native human insulin B chain residues 9 to 23 due to amino acid substitutions at residues 16 and 19, wherein the peptide analogue is capable of reducing incidence of diabetes in non-obese diabetic (NOD) mice, and wherein the peptide analogue consists of no more than 18 residues of human insulin B chain.

21. The peptide analogue of claim 20, wherein residues 16 and 19 are substituted with Ala.

22. A pharmaceutical composition comprising a peptide analogue according to claim 20 or 21 in combination with a physiologically acceptable carrier or diluent.

* * * * *

SEQUENCE LISTING

```
<160> NUMBER OF SEQ ID NOS: 2

<210> SEQ ID NO 1
<211> LENGTH: 30
<212> TYPE: PRT
<213> ORGANISM: Homo sapiens
<220> FEATURE:
<223> OTHER INFORMATION: Human Insulin B Chain

<400> SEQUENCE: 1

Phe Val Asn Gln His Leu Cys Gly Ser His Leu Val Glu Ala Leu Tyr
 1               5                   10                  15

Leu Val Cys Gly Glu Arg Gly Phe Phe Tyr Thr Pro Lys Thr
            20                  25                  30

<210> SEQ ID NO 2
<211> LENGTH: 15
<212> TYPE: PRT
<213> ORGANISM: Homo sapiens
<220> FEATURE:
<223> OTHER INFORMATION: Residues 9-23 of human insulin B chain

<400> SEQUENCE: 2

Ser His Leu Val Glu Ala Leu Tyr Leu Val Cys Gly Glu Arg Gly
 1               5                   10                  15
```